US012011234B2

(12) United States Patent
Noonan et al.

(10) Patent No.: US 12,011,234 B2
(45) Date of Patent: *Jun. 18, 2024

(54) DOCKING DEVICE FOR OPTICAL SHAPE SENSING LAUNCH FIXTURES

(71) Applicant: KONINKLIJKE PHILIPS N.V., Eindhoven (NL)

(72) Inventors: David Paul Noonan, New York, NY (US); Molly Lara Flexman, Melrose, MA (US); Bharat Ramachandran, Morganville, NJ (US); Merel Danielle Leistokow, Vleuten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,506

(22) Filed: Aug. 12, 2022

(65) Prior Publication Data

US 2022/0378519 A1 Dec. 1, 2022

Related U.S. Application Data

(63) Continuation of application No. 16/252,920, filed on Jan. 21, 2019, now Pat. No. 11,432,880, which is a
(Continued)

(51) Int. Cl.
*A61B 34/20* (2016.01)
*A61B 90/57* (2016.01)
(Continued)

(52) U.S. Cl.
CPC .............. *A61B 34/20* (2016.02); *A61B 90/57* (2016.02); *A61B 90/98* (2016.02); *G02B 6/3624* (2013.01);
(Continued)

(58) Field of Classification Search
CPC ...... A61B 2034/2061; A61B 2090/571; A61B 2560/0456; A61B 34/20; A61B 90/57;
(Continued)

(56) References Cited

U.S. PATENT DOCUMENTS 4,325,607 A 4/1982 Carlsen
4,373,779 A 2/1983 Glenn
(Continued)

FOREIGN PATENT DOCUMENTS

JP H05505119 8/1993
JP 3157855 10/1993
(Continued)

*Primary Examiner* — Michael T Rozanski

(57) ABSTRACT

An optical shape sensing (OSS) system includes a launch fixture configured to receive and secure an optical fiber within a flexible OSS enabled instrument, where the launch fixture includes a docking interface; a launch fixture base configured to be connected to a support structure; and a docking device configured to secure the launch fixture onto the launch fixture base. The docking device includes a launch fixture slot passing through the docking device, and the launch fixture slot is configured to receive and secure the docking interface of the launch fixture through both a top side of the docking device and an opposing bottom side of the docking device.

20 Claims, 20 Drawing Sheets

Related U.S. Application Data continuation-in-part of application No. 15/021,047, filed as application No. PCT/IB2014/064361 on Sep. 10, 2014, now abandoned.

(60) Provisional application No. 61/884,178, filed on Sep. 30, 2013.

(51) Int. Cl.
 *A61B 90/98* (2016.01)
 *G02B 6/36* (2006.01)

(52) U.S. Cl.
 CPC . *A61B 2034/2061* (2016.02); *A61B 2090/571* (2016.02); *A61B 2560/0456* (2013.01)

(58) Field of Classification Search
 CPC .... A61B 90/98; G02B 6/3624; G02B 6/3897; G02B 6/4441
 See application file for complete search history.

(56) References Cited

U.S. PATENT DOCUMENTS

| | | |
|---|---|---|
| 7,720,322 B2 | 5/2010 | Prisco |
| 8,146,591 B2 | 4/2012 | Niklewski |
| 8,465,476 B2 | 6/2013 | Rogers |
| 9,259,278 B2 | 2/2016 | Jensen |
| 9,358,358 B2 | 6/2016 | Wondka |
| 11,432,880 B2* | 9/2022 | Noonan .................. A61B 90/98 |
| 2004/0037509 A1 | 2/2004 | Wisecarberg |
| 2008/0105318 A1 | 5/2008 | Leone |
| 2011/0091160 A1 | 4/2011 | He |
| 2011/0202069 A1 | 8/2011 | Prisco |
| 2012/0224823 A1 | 9/2012 | Cox |
| 2013/0030363 A1 | 1/2013 | Wong |
| 2013/0204072 A1 | 8/2013 | Verard |
| 2013/0317356 A1 | 11/2013 | Ramachandran |
| 2014/0308016 A1 | 10/2014 | Ramachandran |
| 2017/0071683 A1 | 3/2017 | Prisco |

FOREIGN PATENT DOCUMENTS

| | | |
|---|---|---|
| JP | 2006126041 | 5/2006 |
| JP | 2011104053 | 6/2011 |
| JP | 2011156217 | 8/2011 |

* cited by examiner

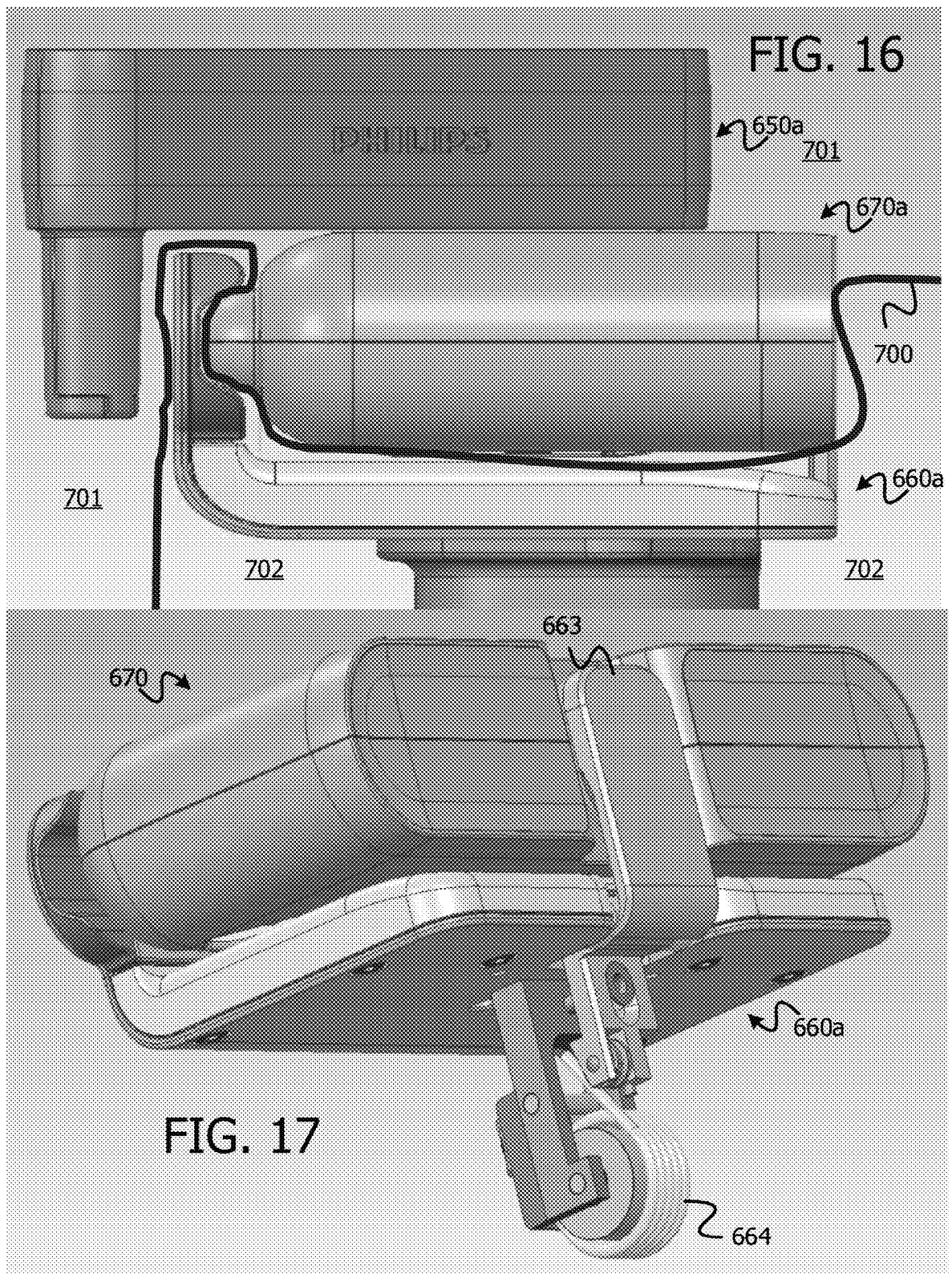

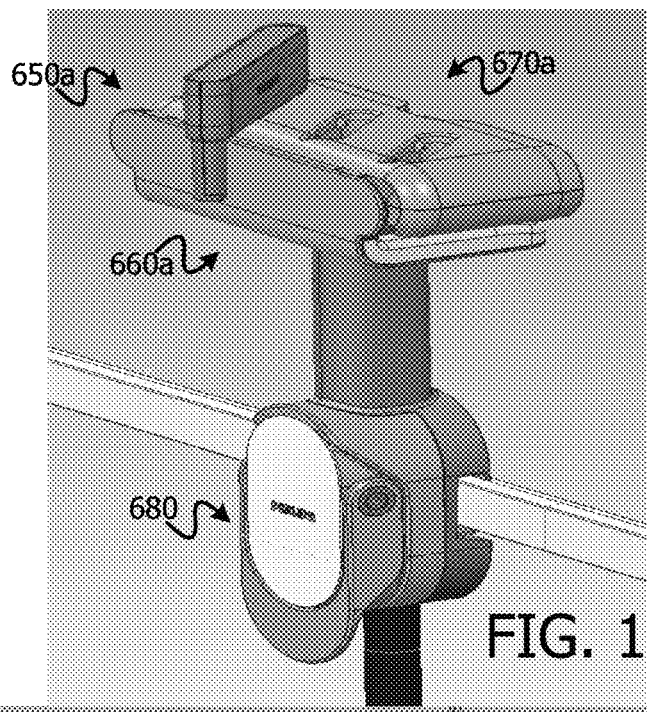
FIG. 18A
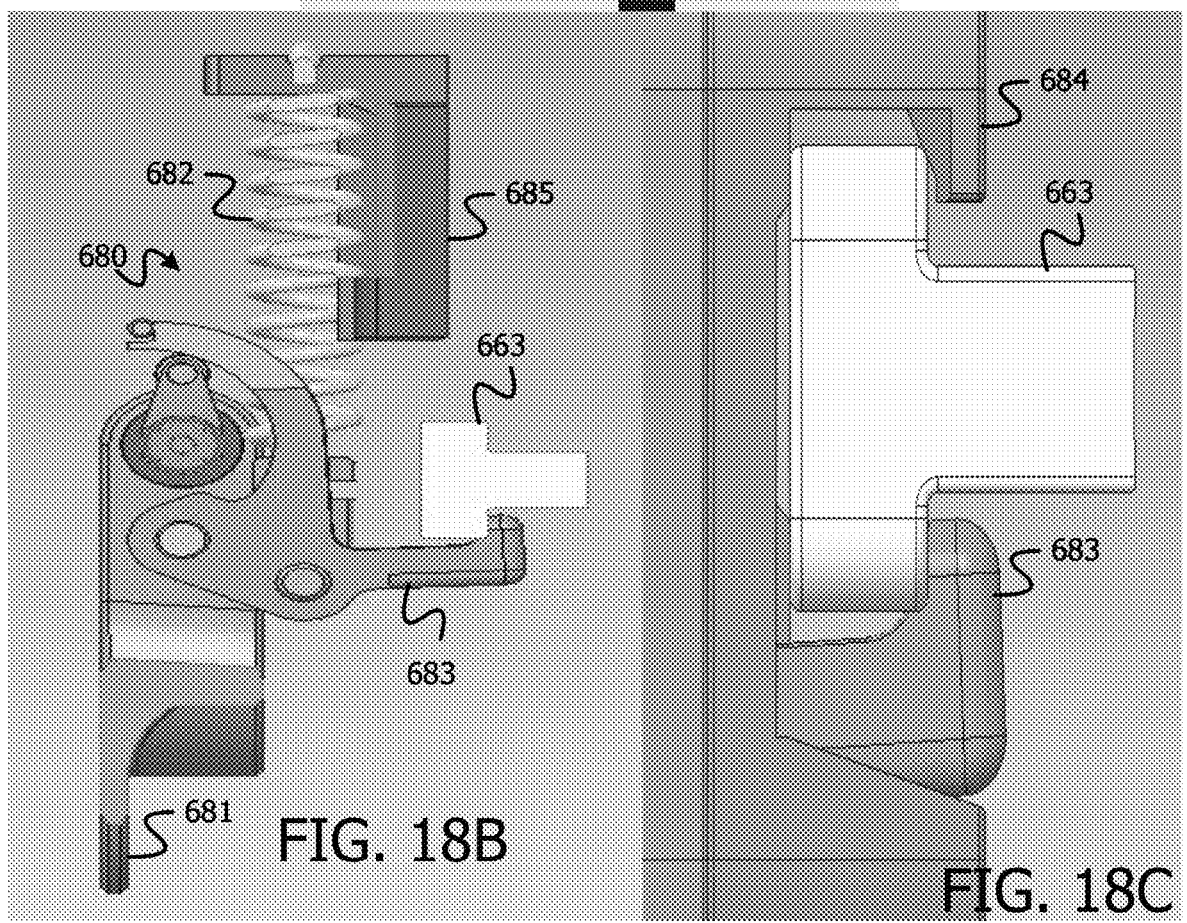
FIG. 18B
FIG. 18C

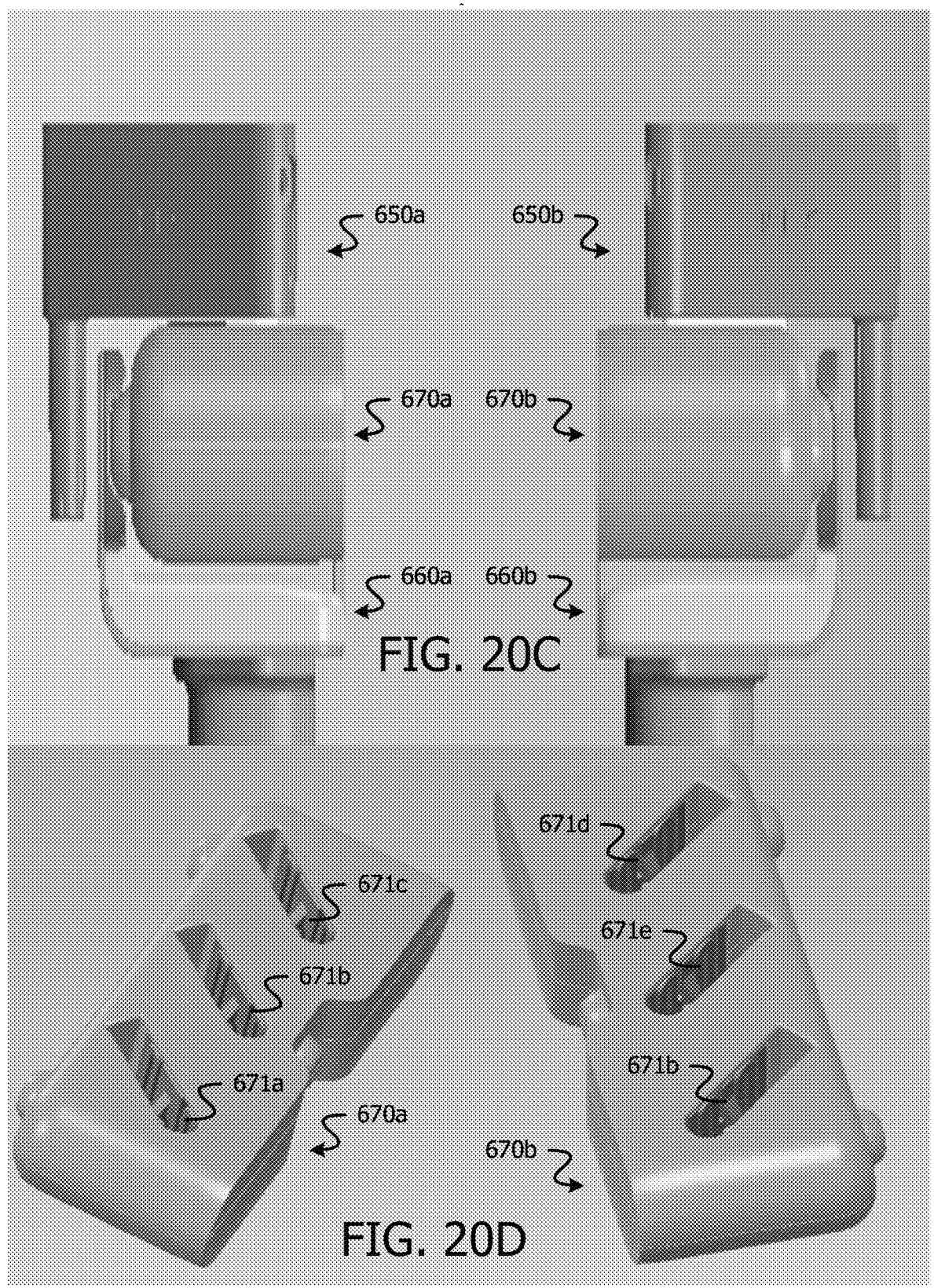

DOCKING DEVICE FOR OPTICAL SHAPE SENSING LAUNCH FIXTURES

CROSS REFERENCE TO PRIOR APPLICATIONS

This application is a Continuation application of U.S. Ser. No. 16/252,920 filed Jan. 21, 2019, which is a Continuation-In-Part application of U.S. Ser. No. 15/021,047 filed Mar. 10, 2016 (abandoned), which is a U.S. National Phase application under 35 U.S.C. § 371 of International Application No. PCT/IB2014/064361 filed on Sep. 10, 2014, which claims the benefit of U.S. Provisional Application No. 61/884,178 filed on Sep. 30, 2013. These applications are hereby incorporated by reference in their entireties.

BACKGROUND

Technical Field

This disclosure relates to medical instruments and more particularly to shape sensing optical fibers in medical applications.

Description of the Related Art

Optical shape sensing (OSS) is a technology that permits accurate three-dimensional (3D) reconstruction of a shape of a fiber along its entire length. Integrating the fiber into an OSS enabled instrument requires coupling the fiber to the instrument such that any movement of the device can be reconstructed with respect to a fixed frame of reference. Having a fixed or static launch region is needed since the fixed region provides a search template for a reconstruction algorithm to perform correlation and to match a reference to sample data. The reconstruction initializes after this fixed region. The fixed region also defines the frame of reference (0,0,0) for OSS and, in essence, the coordinate system in the shape sensing space.

SUMMARY

In accordance with the present principles, a launch fixture for optical shape sensing (OSS) includes a first fixation device configured to receive and secure an optical fiber. A fiber storage area is configured to receive and maintain the optical fiber within specified dimensions. A second fixation device is configured to receive and secure a flexible OSS enabled instrument. A launch region is configured to receive and maintain the optical fiber in a known geometric configuration before entering the second fixation device. A feature is provided for aligning and coupling to a launch fixture base, which is configured to secure the launch fixture.

An optical shape sensing (OSS) system includes a launch fixture base configured to be connected to a support structure, and a launch fixture configured to be secured on the launch fixture base by at least one feature for aligning and coupling the launch fixture base to the launch fixture. The launch fixture includes a first fixation device configured to receive and secure an optical fiber; a fiber storage area configured to receive and maintain the optical fiber within specified dimensions; a second fixation device configured to receive and secure a flexible OSS enabled instrument; and a launch region configured to receive and maintain the optical fiber in a known geometric configuration before entering the second fixation device.

A method for optical shape sensing (OSS) includes providing (502) a launch fixture having a first fixation device configured to receive and secure an optical fiber, a fiber storage area configured to receive and maintain the optical fiber within specified dimensions, a second fixation device configured to receive and secure a flexible OSS enabled instrument, a launch region configured to receive and maintain the optical fiber in a known geometric configuration before entering the second fixation device, and at least one feature for aligning and coupling to a launch fixture base, which is configured to secure the launch fixture; and sensing a shape of the optical fiber.

The launch fixture may include features for aligning and coupling the launch fixture to a launch fixture base, which is configured to secure the launch fixture.

Alternatively, a docking device may be provided for securing one or more launch fixtures onto the launch fixture base whereby the docking device may serve as a bridge between a sterile zone and a non-sterile zone. The docking device may include one or more launch fixture slots on one side of the docking device, or one or more launch fixture slots on each of two opposing sides of the docking device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 16 is a perspective view of a launch base cover claim in accordance with one embodiment;

FIG. 17 is a perspective view of a docking clamp of the launch fixture base in accordance with one embodiment;

FIGS. 18A-18C are a perspective view and a side view, respectively, of support clamp in accordance with one embodiment;

FIGS. 20A-20E are views of the shape sensing system employing two sets of launch fixtures relative to a patient in an operating environment in accordance with one embodiment.

DETAILED DESCRIPTION OF EMBODIMENTS

Figure 1:
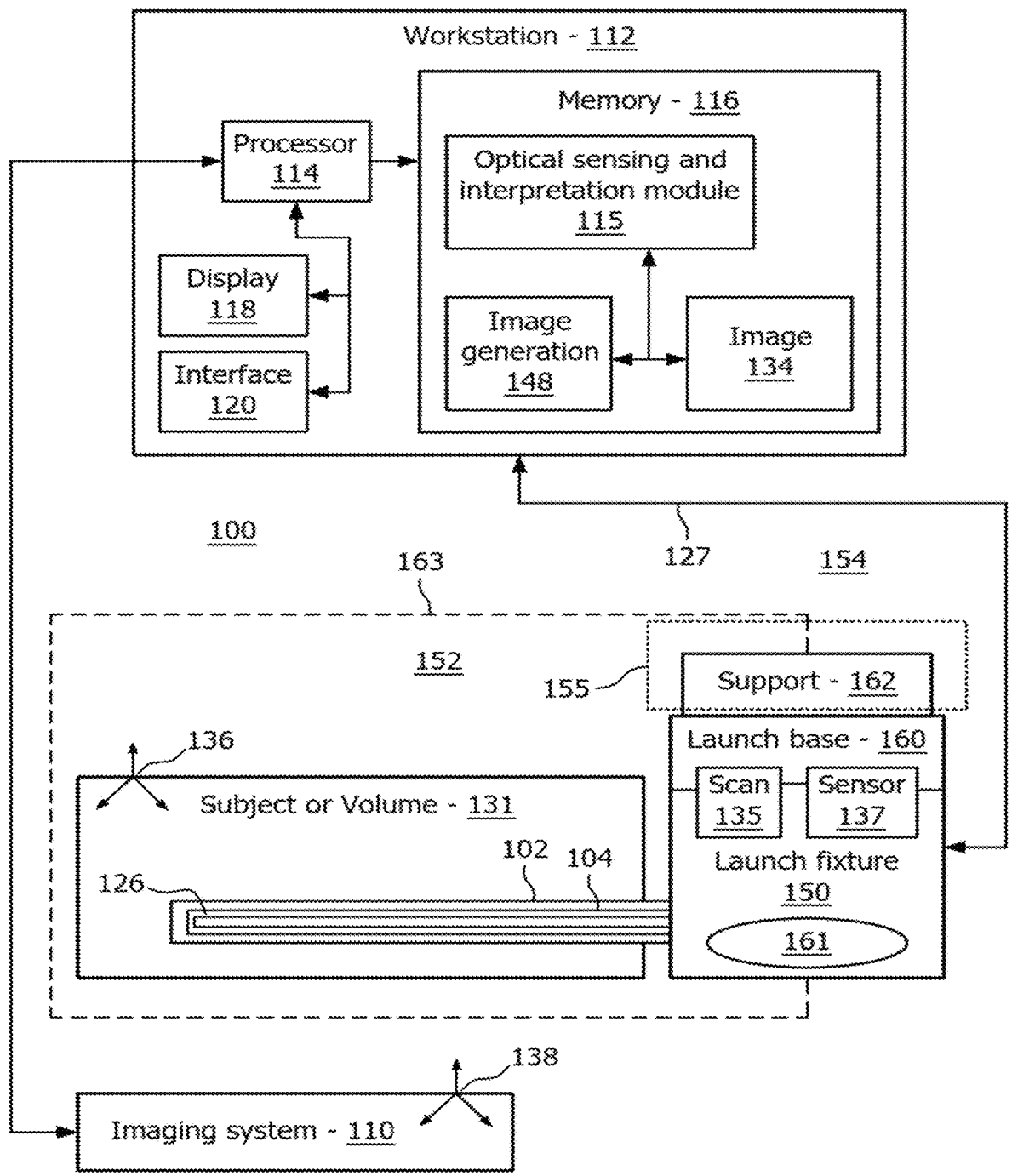
FIG. 1 is a block/flow diagram showing a shape sensing system which employs a launch fixture with controlled fiber positioning in accordance with one embodiment.

In accordance with the present principles, a launch fixture and launch fixture base design provide for rapid attachment and detachment of one or more optical shape sensing (OSS) enabled flexible instrument(s) to a fixed reference in an operating theatre. The fixture can also be disposed in a transition zone between sterile and non-sterile regions in an operating theatre, allowing for the rapid exchange of OSS-enabled devices by personnel in the non-sterile region without breaking the sterile barrier.

In one embodiment, the launch fixture ensures that the geometric relationship between adjacent instrument frames of reference and the launch fixture base frame of reference are known, so that each instrument is automatically registered to the launch fixture base once connected. Given that the launch fixture base is registered to a patient or imaging frame of reference prior to a beginning of the procedure, this architecture permits each instrument to be rapidly deployed in a co-registered frame of reference. In addition, the overall footprint of the instruments in the operating theatre can be minimized through the use of vertical, horizontal, or angled stacking.

During clinical use, it is likely that multiple shape sensing enabled instruments will be deployed and exchanged during a given procedure. In one system architecture, each instrument could be attached to the operating table using a unique launch fixture base. However, as the number of instruments employed increases, a number of components attached to the table would increase accordingly. This would hinder clinician movement around the table and result in a cluttered operating field. In addition, since the OSS fiber within each instrument will reconstruct the shape of the instrument with respect to a frame of reference located within that instruments' launch fixture, each instrument would need to be individually registered to the patient/imaging system frame of reference.

In accordance with the present principles, the footprint of the instrument launch fixtures within the operating theatre is minimized, as well as the time spent registering devices. The launch fixture and launch fixture base permit rapid exchange of devices while maintaining a defined geometric relationship between frames of reference so that re-registration is not required. This fixed frame of reference is included within a launch fixture, which is coupled to a proximal end of the flexible instrument and includes design features which allow the fiber to be safely and securely coupled to the instrument. By attaching this launch fixture rigidly to the launch fixture base, which may itself be rigidly connected to the operating table, needed transformations between an instrument frame of reference and patient/imaging frames of reference can be computed. Thus, the reconstructed shape of the instrument can be overlaid on pre- and intra-operative images and used for navigation purposes.

It should be understood that the present invention will be described in terms of medical instruments; however, the teachings of the present invention are much broader and are applicable to any fiber optic shape sensed instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for optical shape sensing is illustratively shown in accordance with present embodiments. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device or system 104. Optical sensing module 115 is configured to use the optical signal feedback (and any other feedback, e.g., electromagnetic (EM) tracking) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

The shape sensing system 104 on device 102 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In one embodiment, workstation 112 includes an image generation module 148 configured to receive feedback from the shape sensing device 104 and display position/shape for the shape sensing device 104 within a volume 131. An image 134 of the shape sensing device 104 within the space or volume 131 can be displayed on a display device 118. Workstation 112 includes the display 118 for viewing internal images of a subject (patient) or volume 131 and may include the image 134 as an overlay or other rendering of shapes of the shape sensing device 104. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A launch fixture 150 includes mechanical features 152 configured to ensure that the fiber 126 or the shape sensing device 104 can be coupled to the elongate instrument 102 such that the fiber measures changes in shape of the instrument with respect to a fixed frame of reference. Each OSS enabled instrument 102 employs a launch fixture (150) to define a fixed frame of reference which may be registered to a patient frame of reference 136, or imaging frame of reference 138, or both.

A launch fixture base 160 is rigidly attached to a fixed feature or support structure 162 in the operating theatre (e.g., an operating table or similar structure) which allows for multiple launch fixtures 150 (and hence multiple OSS enabled instruments 102) to be attached and co-registered to the patient frame of reference 136, or imaging frame of reference 138, or both. In another embodiment, there is more than one OSS enabled instrument 104 within a single fixture 150. The launch and coordinate systems of these fibers are known with respect to each other as well as the patient and imaging frames of reference 136, 138, thus allowing faster use when these devices are used in conjunction, such as, e.g., a guidewire and a catheter being used together.

In another embodiment, the launch base 160 and/or the launch fixture 150 may include features to monitor the use of the launch fixture 150 and devices 102. For example, a scan mechanism 135 may be incorporated into the base 160 or fixture 150 (e.g., a radiofrequency scanner) that automatically detects which OSS enabled instrument 102 is being used. Mechanism 135 may monitor a number of times a same device is clipped in (to monitor or prevent) more than one-time use of the device 102. The mechanism 135 may include an indicator (e.g., a light, counter or color strip) that indicates an end of life (after say 1000 devices have been mounted) of the launch base 150 and alert the service engineer for maintenance. Other configurations for mechanism 135 are also contemplated.

In one embodiment, a position of the launch fixture base 160 (and/or launch fixture 150) with respect to an imaging system 110 is tracked using an appropriate sensor 137 (position encoder, magnetic tracking, etc.). This provides easy registration to the imaging system 110.

Another feature of the launch fixture 150 is that it may lay in a zone separating a sterile region 152 (inside the dashed box) and a non-sterile region 154 in a surgical room. A sterile barrier 163 may be provided such that a proximal portion of device 150 (in region 154) is non-sterile and a distal portion of the device 150 (in region 154) is in the sterile region, which includes a mechanism (a barrier or sealed partition within the device 150) for not contaminating the sterile region 152 in an operating room. In one possible workflow, by allowing the non-sterile personnel such as a nurse to perform the proximal connections to a laser and clip on the launch fixture 150 to the launch base 160 and handing a protected OSS-enabled instrument 104 to the sterile personnel, the launch fixture 150 allows use of OSS-enabled devices 104 without breaking the sterile barrier. In another possible workflow, the launch base 160 is also sterile and connects to the support 162 over a sterile drape 155. This combination also allows for the launch fixture 150 to be employed to enable the use of OSS instruments 102 without breaking the sterile barrier 163.

Figure 2:
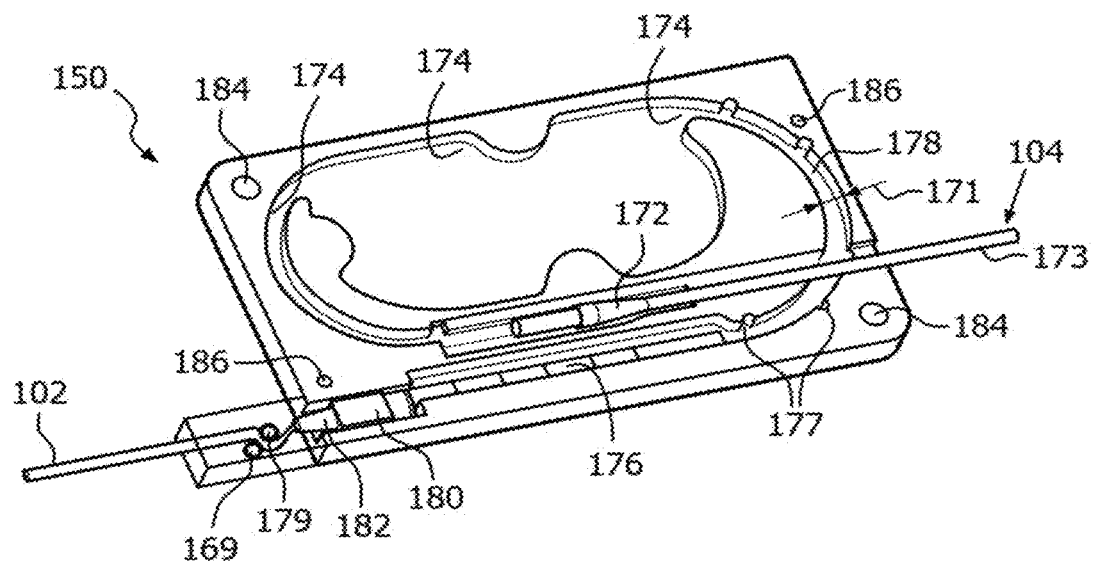
FIG. 2 is a perspective view of a launch fixture with controlled fiber positioning in accordance with one embodiment.

Referring to FIG. 2, a launch fixture 150 suitable for coupling an OSS fiber device 104 to a flexible instrument 102 in a controlled manner is illustratively shown. The launch fixture 150 includes a fixation point or device 172 to clamp the optical fiber 104 and its protective tubing, housing, or similar structure 173 in place into the fixture 150. A defined path 174 is formed to permit excess fiber to be included within the fixture 150 while not exceeding a specified minimum bend radius. This path 174 may also include features which allow for automatic alignment of the polarization of the OSS laser system to be performed while the instrument is connected to the OSS console. When a fiber undergoes a tight bend the index of refraction experienced by the light through that bend will vary depending on the orientation of the light. To mitigate these birefringence effects, optical shape sensing measurements are commonly performed with multiple light polarizations. One technique to optimally select (or 'align') those polarization states is to use the measured optical response through a known feature, such as a bend. An example of such a feature is a defined path 174 with sufficient curvature to induce birefringence effects in the fiber. These birefringence effects provide unique features in the measured optical signal that can be used for automatic alignment of the system polarization. Ideally, this curvature will have a tight radius to amplify the birefringence effects and thus allow for a more unique feature upon which to perform alignment. This alignment feature can exist prior to a launch region 176 within the launch fixture 150.

The launch region 176 permits the OSS fiber device 104 to be physically attached to the fixture 150 in a defined manner (e.g., straight or with a known geometry). The path prior to the launch region 176 may have features 177 which ensure the fiber enters the launch region 176 in a controlled manner (e.g., pegs, radiused features, etc.). A path 178 (which may be included in path 174) acts as a buffer, or service loop, to allow for curvature induced path length changes to be accommodated by the fiber repositioning within the fixture 150 while not exceeding a specified minimum bend radius. Such a service loop may take several different forms, e.g., the service buffer loop of path 178 may include a 90 degree, 360 degree bend, etc. instead of or in addition to the 180 degree bend depicted in FIG. 2. A gap distance 171 of the path 178 provides slack for manipulating the fiber but protects the fiber from exceeding the minimum bend radius.

A fixation point or device 180 clamps the flexible instrument 102 to the fixture 150 and surface curvatures/fillets 182 ensure that the transition between the fixture 150 and the flexible instrument 102 occurs without negatively effecting the strain measurement of the OSS fiber 104. Mechanical design features 184 allow the fixture 150 to be reproducibly connected to the launch fixture base 160 (FIG. 1), or other launch fixtures in a known geometric manner. Screws, magnets, snap-fits, clips, pegs, or similar mechanisms can be employed to achieve this. Feature or features 184 with known geometry, curvature or shape, may be employed for registering the device 102 to other OSS-enabled devices, the patient and the imaging frame of reference 136, 138. The feature(s) 184 may be employed for the dual purpose of attaching the fixture 150 to the launch base 160 and attaching fixtures 150 to each other. The feature(s) 184 may be directional shaped (e.g., square, triangle, etc.) to ensure that the base 160 and the fixtures 150 are properly aligned relative to one another.

The launch fixture 150 is depicted in an open configuration in FIG. 2. A lid (not shown) can be employed to cover the open launch fixture 150 or another launch fixture (not shown) may nest or be coupled to the launch fixture 150. The lid or additional launch fixture (150) may be screwed or otherwise connected into place to both clamp the components into place (on the base 160) and to protect the fiber from the environment by employing features 186. Feature 186 may include similar mechanism and described for features 184.

An additional feature of the launch fixture 150 includes a defined path 179 for the fiber distal from the launch region 176 which can be used to correct for any rotation of the launch region during use. In practice, the fiber is clamped in place at the launch region 176; however, in some circumstances the fiber can 'rotate' within the clamp and thus any registrations can become inaccurate. By having a known shape distal from the launch region, this rotation can be corrected for. The defined path 179 may include a curved path in two or three dimensions, e.g., a semi-circle, compound curves (e.g., sinusoid), an arc, a coiled shape, etc. The defined path 179 may be included distally to the launch region 176 within the launch fixture 150 or may be included as a detachable module 169 that connects to the launch fixture (as depicted in FIG. 2).

Figure 3:
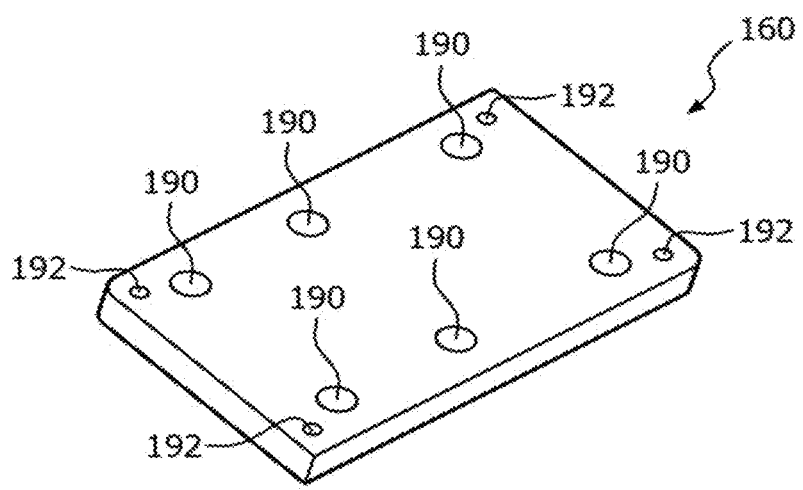
FIG. 3 is a perspective view of a launch fixture base configured to secure one or more launch fixtures in accordance with one embodiment.

Referring to FIG. 3, a launch fixture base 160 is shown in accordance with one illustrative embodiment. The launch fixture base 160 includes features 190, such as holes, pegs, detents, protrusions, etc. configured to rigidly attach to a fixed frame of reference within the operating theatre (e.g., the operating table or the like). The launch fixture base 160 includes the ability to be reproducibly connected to one or more launch fixtures 150 with a known geometric relationship. This may include features 192, such as holes, pegs, detents, protrusions, etc. configured to permit easier connection and fixation of the launch fixture(s) 150 or a lid on the launch fixture(s) 150.

Figure 4:
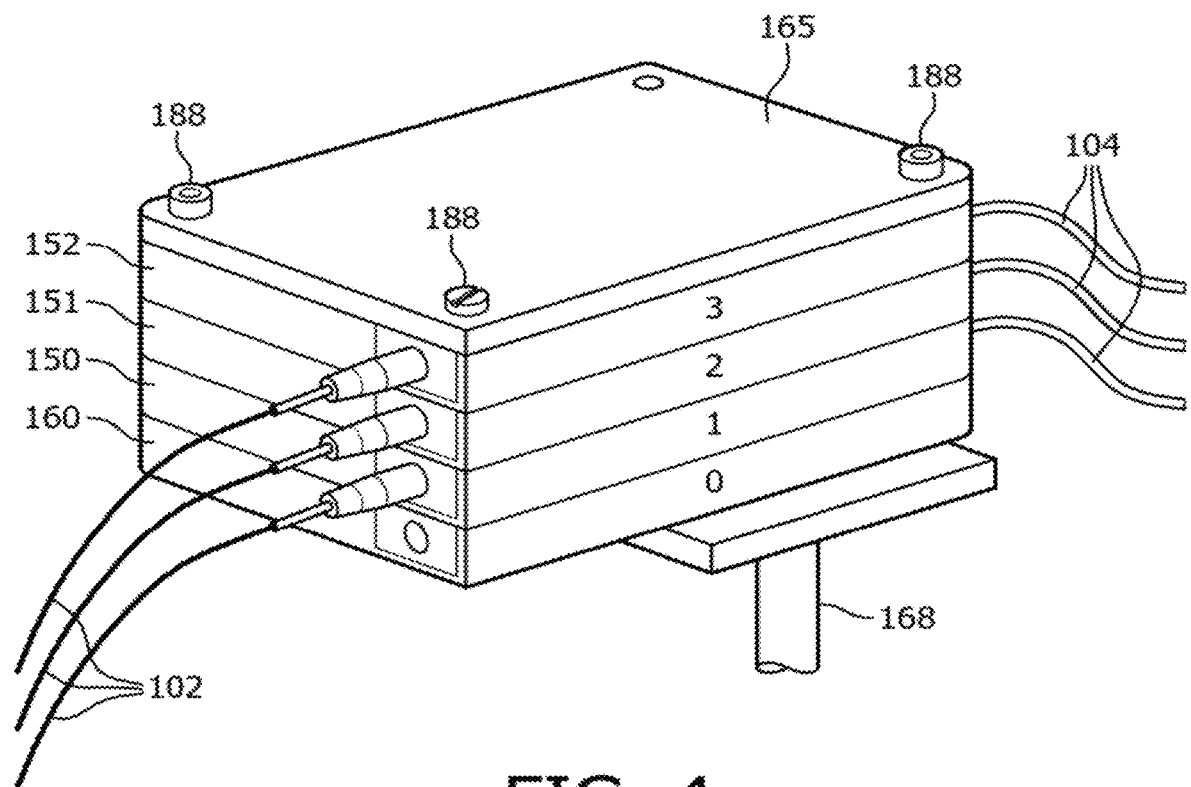
FIG. 4 is a perspective view showing a plurality of stacked launch fixtures with controlled fiber positioning in accordance with one embodiment.

Referring to FIG. 4, three launch fixtures 150, 151 and 153 are connected to a launch fixture base 160 which is, in turn, connected to an operating table (not shown) via steel rods and support structure 163 and appropriate clamps, etc. In this architecture, the transformations between the frames of reference of the individual launch fixtures (and hence the flexible instruments 102 connected to the launch fixtures 150, 151, 153) and the launch fixture base 160 are known. Assuming a transformation between the launch fixture base 160 and the patient or imaging system frame of reference is known, then different launch fixtures 150, 151, 153 can be connected to the launch fixture base 160 and used for imaged guided navigation without requiring a re-registration step. The known geometric relationship between each launch fixture 150, 151, 153 and the launch fixture base 160 can be used to minimize time spent registering each device to the patient/imaging system frame of reference.

In one embodiment, launch fixtures 150, 151, 153 can be rigidly attached to the launch fixture base 160 using threaded bolts 188. A lid 165 may be employed as well and secured together with fixtures 150, 151, 153. For example, additional launch fixtures 151, 153 can be attached to the initial launch fixture 150 with lid 165 using longer bolts. In other embodiments, magnets, clips, snap fits or similar rapid attachment components may be employed instead of bolts to attach and detach the launch fixture(s) from each other and the launch fixture base 160. Quick connect or magnetic attachment mechanisms (e.g., snap together arrangements, clamps, clasps, tongue and groove, etc.) may be employed to make quick and secure but releasable connections between the base 160 and fixtures 150, 151, 153 and between fixtures 150, 151, 153. The geometric relationship between adjacent launch fixtures 150, 151, 153 (and hence their instrument frames of reference) and the launch fixture base 160 can be used to ensure that re-registration of multiple devices is not required as devices are exchanged during a procedure. In addition, by locating the fixtures 150, 151, 153 and base 160 at a single location clutter is reduced and an organized and efficient operating theater is maintained.

Figure 5:
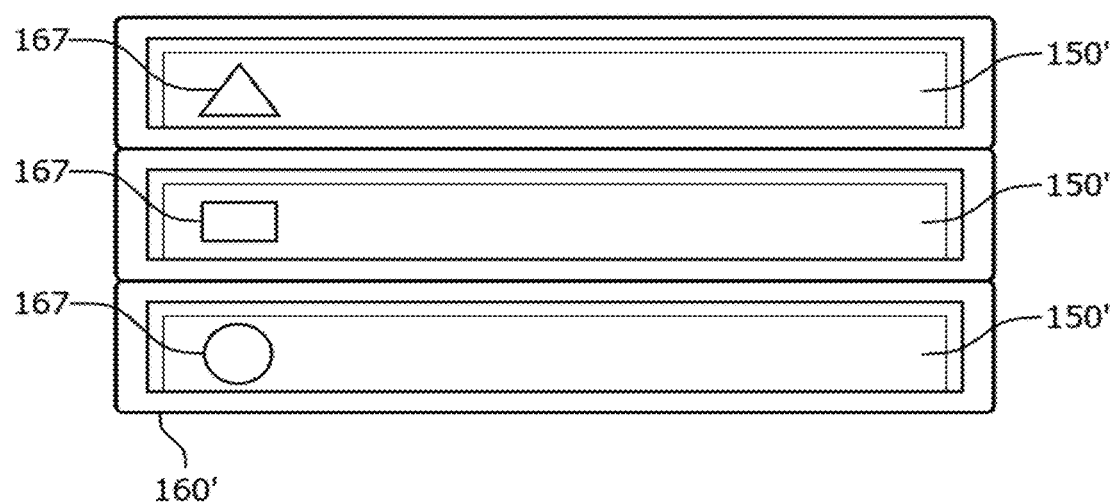
FIG. 5 is a side view of a launch fixture base rack for storing a plurality of launch fixtures in accordance with one embodiment.

Referring to FIG. 5, in another embodiment, launch fixtures 150' couple to a launch fixture base 160' independently (e.g., not stacked on each other). Examples of such an embodiment include a rack-style base or similar architecture where the fixtures can be stacked horizontally, vertically or angled with respect to an operating table or other reference structure.

In one embodiment, connection features 163 may include different shapes for receiving different types of OSS enabled devices 102. For example, a square, triangle, circle, etc. feature 163 may be employed to limit the type of OSS enabled device 102 connected to the launch fixture 150'. For example, a guide wire may include a square connector, a catheter may include a round connector and an endoscope may include a triangular connector.

Figure 6:
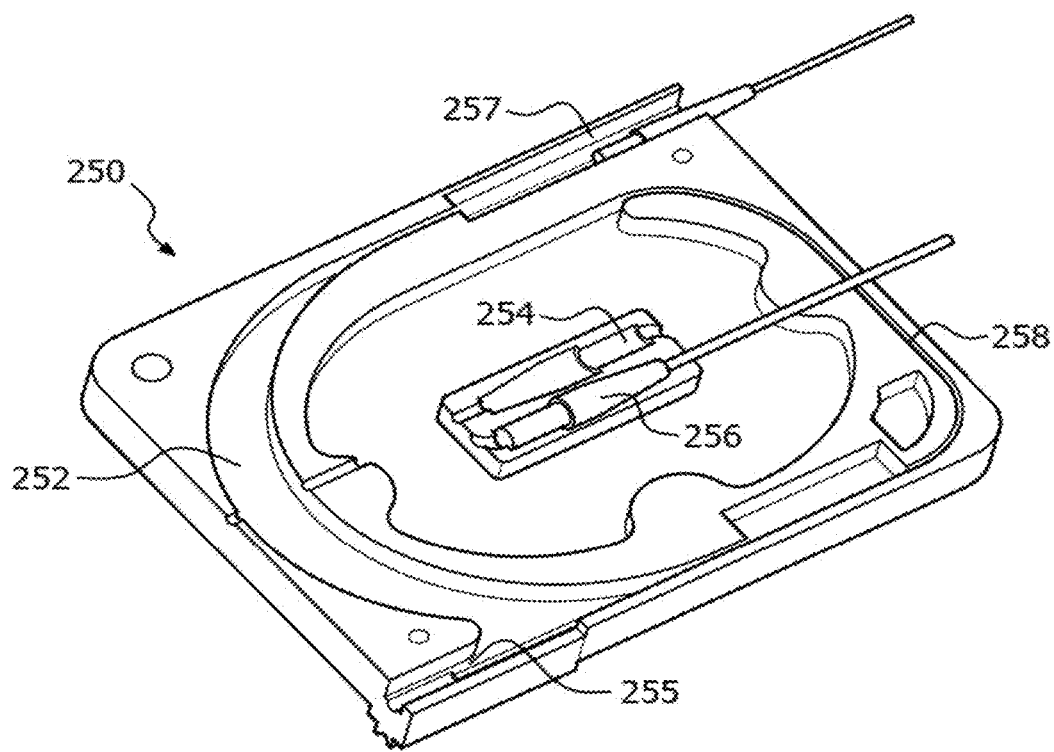
FIG. 6 is a perspective view of a launch fixture for handling a plurality of shape sensing devices with controlled fiber positioning in accordance with another embodiment.

Referring to FIG. 6, in another embodiment, similar to that launch fixture 150, a launch fixture 250 is shown capable of coupling two OSS fibers 104 to two flexible instruments 102 within a single fixture 250. An entrance point 254 for one fiber and an exit point 255 for one flexible instrument 102 are depicted. An entrance point 256 for one fiber and an exit point 257 for another flexible instrument 102 are also depicted. In this embodiment, if two instruments 102 are employed within the single fixture 250, one instrument 102 may use a buffer, or service loop 252 and, the other instrument 102 may not employ the service loop 252. However, a service loop may be provided for both instruments in other embodiments. Other embodiments may employ a single fixture with a greater number of flexible instruments. A fiber path 258 may be employed for automatic alignment of light source polarization states, as described above.

Figure 7:
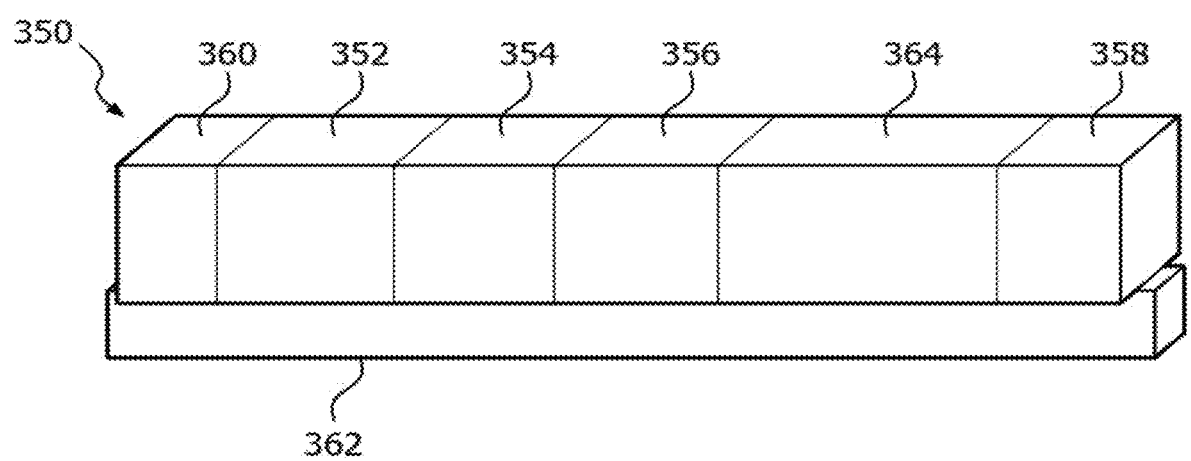
FIG. 7 is a perspective view of a modular launch fixture with attachable/detachable modules in accordance with one embodiment.

Referring to FIG. 7, a modular launch fixture 350 is shown in accordance with one embodiment. The fixture 350 illustratively includes selected elements or features needed to couple an OSS fiber to a flexible instrument in a controlled manner. The launch fixture 350 in this particular embodiment adopts a modular approach to attaching each of a plurality of elements described above to a rail system or launch fixture base 362. This rail 362 can be attached to an operating table and then registered to the patient and/or imaging system frame of reference.

The launch fixture 350 illustratively includes a launch region module 352, a buffer or service loop module 354, an excess fiber path module 356, a fiber boot clamp module 358, and a clamp module 360 for the flexible instrument 102. Other modules 364 may be included. The modules 352, 354, 356, 358, 362, 364 are individually separable from the launch fixture base 360 and adjacent modules. The modular embodiment of the launch fixture 350 may include multiple flexible instruments and/or stackable launch fixtures, each with one or more flexible instruments. The fibers in each module may include optical connectors so that modules can be easily changed out as needed.

Figure 8A:
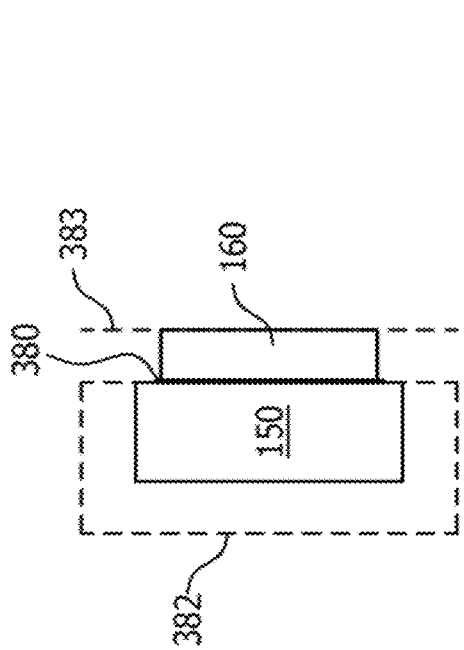
FIG. 8A is a side view showing a sterile boundary between a launch fixture and a launch fixture base in accordance with one embodiment.

Referring to FIG. 8A, a protective layer 380 (e.g., a plastic film, sterile drape or the like) is disposed between the launch base 160 and the launch fixture 150, allowing a sterile device within a protected plastic 382 to clip on the non-sterile launch-base 160 while still having the packaging that maintains sterility. Others arrangements are also contemplated.

In another embodiment, the launch fixture base 160 can be multi-use, sterilizable and connect over a sterile drape 383. The launch fixture 150 can be connected to the sterile launch fixture base 160 thus allowing the OSS device to be used within the sterile field.

Figure 8B:
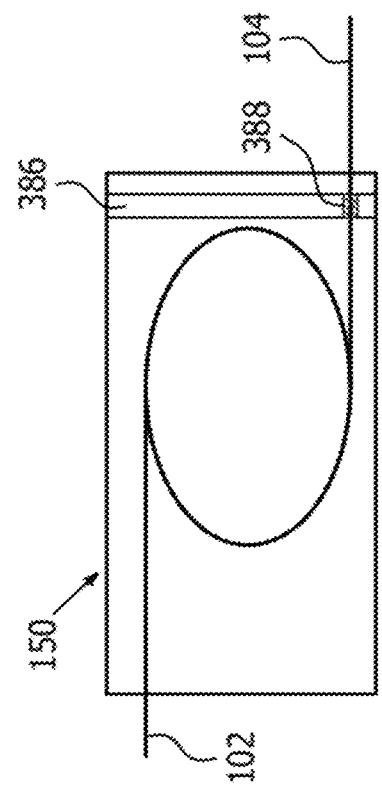
FIG. 8B is a top view showing an open launch fixture with a partitioned sterile boundary between distal and proximal portions of the launch fixture in accordance with one embodiment.

Referring to FIG. 8B, a protective partition 386 (e.g., a stainless steel wall) with sealed orifices 388 is disposed in the launch fixture 150, allowing a sterile device on a distal side (with instrument 102) and a non-sterile device on a proximal side (with fiber 104). Others arrangements are also contemplated.

Figure 9:
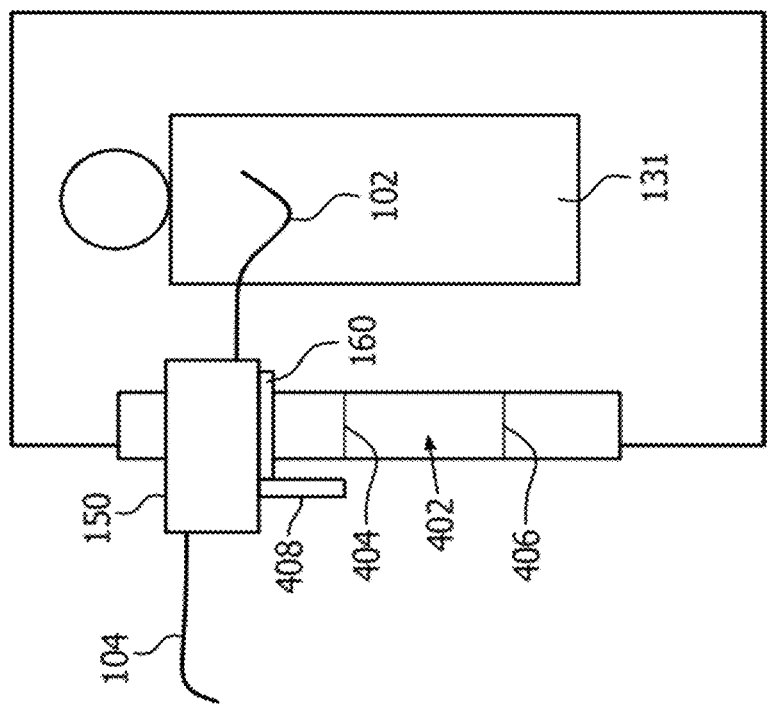
FIG. 9 is a top view of a rail for conveying a launch fixture base in accordance with one embodiment.

Referring to FIG. 9, in another embodiment, the launch fixture base 160 is coupled to a rail 402 or other structure such that the OSS enabled device 102 could be used for entering a body 131 at different locations, such as femoral access versus carotid access. The launch fixture base 160 could be repositioned at preset states or locations 404, 406 and lock into place by a clamp 408 or other securing device. The positions, orientations and transforms of the base 160 at these locations 404, 406 with respect to other locations would be known and thus, registering multiple OSS devices 102 would be straightforward and simple. In one embodiment, the launch fixture 150 and/or launch fixture base 160 may be robotically actuated and manipulated to different positions with or without the rail 402 (the rail 402 may also be robotically positioned). Translation and rotation of the rail 402, the launch fixture 150 and/or launch fixture base 160 may be provided robotically for medical procedures (e.g., endovascular, endoluminal and/or orthopedic applications, etc.) or other applications. In another embodiment, translation along the rail 402 may be performed manually, and the transformations to the patient or imaging coordinate systems, or both, can be calculated by measuring the position along the rail 402 using a position sensing device (potentiometer, optical tracker, etc.). If a robot is employed, the fixtures 150 and base 160 may be registered to the robotic coordinate system.

Figure 10:
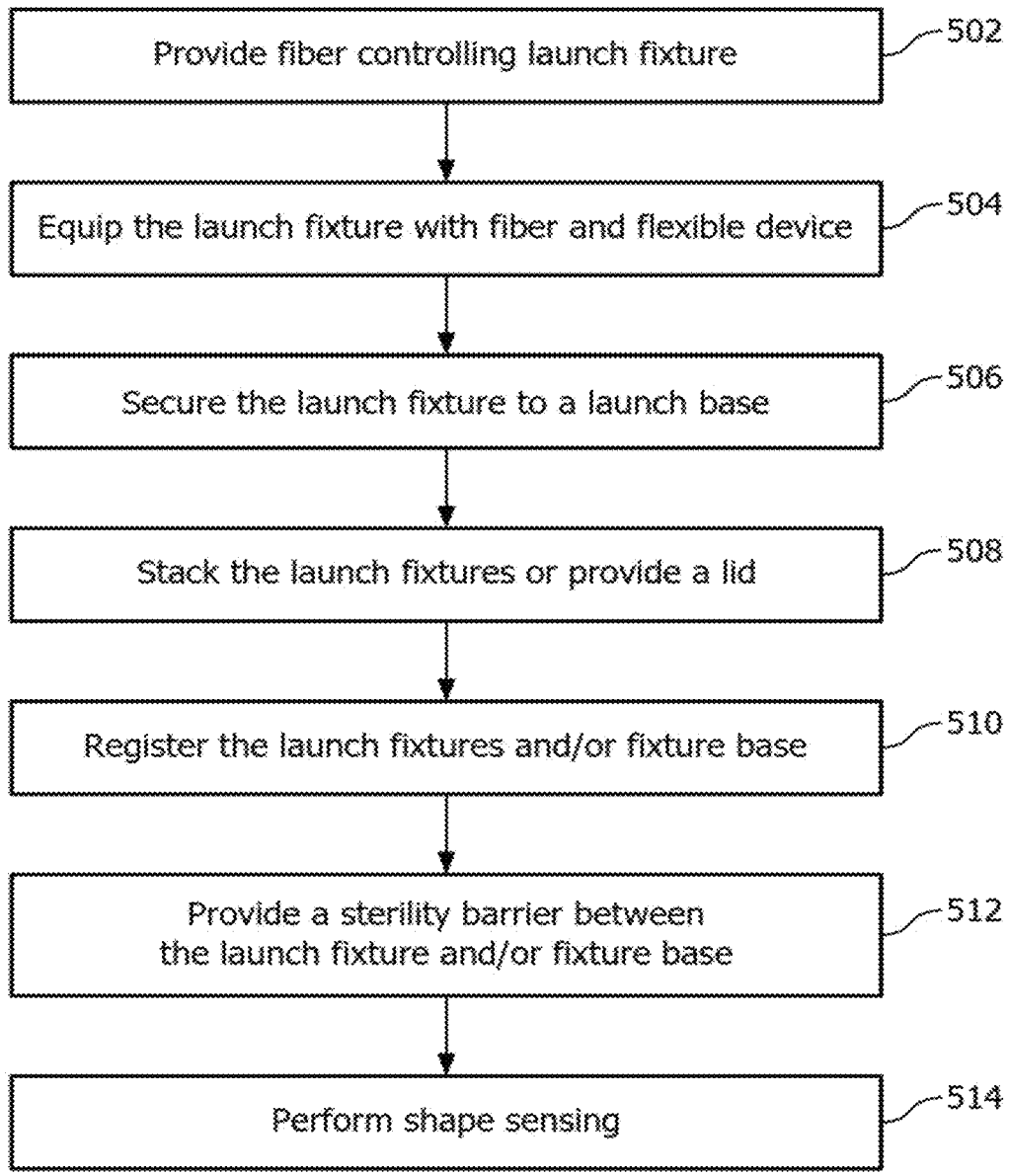
FIG. 10 is a flow diagram showing a method for optical shape sensing in accordance with an illustrative embodiment.

Referring to FIG. 10, a method for optical shape sensing (OSS) includes providing a launch fixture for handling optical fiber in a controlled manner, in block 502. The launch fixture includes a first fixation device configured to receive and secure an optical fiber, a fiber storage area configured to receive and maintain the optical fiber within specified dimensions, a second fixation device configured to receive and secure a flexible OSS enabled instrument, a launch region configured to receive and maintain the optical fiber in a known geometric configuration before entering the second fixation device, and at least one feature for aligning and coupling to a launch fixture base, which is configured to secure the launch fixture. The launch fixture may include other features as well, e.g., a defined path which can be used to correct for rotation of the fiber launch region (as described above).

In block 504, the launch fixture is equipped with at least one OSS fiber, which is initially secured in the first fixation device, and at least one OSS enabled device, which is secured in the second fixation device. The OSS fiber is stowed in buffer or loop area configured to maintain minimum dimensions requirements to the fiber and to provide some slack for accommodating operational movement of the fiber without exceeding the requirements. In block 506, the launch fixture is secured to a launch fixture base. The launch fixture base may be secured to an operating table, a rail system, robotic instrument, imaging system, etc. In one embodiment, the launch fixture base may be actuated to different position within an operating theater.

In block 508, other launch fixtures are stacked on the launch fixture and/or a lid is placed over the launch fixture. In block 510, the launch fixture or fixtures and/or fixture base are registered to at least one of a patient frame of reference and an imaging frame of reference, although other references may be employed. In block 512, a sterile barrier may be employed through the launch fixture(s), between the launch fixture and the launch fixture base or between modules of a modular launch fixture. In block 514, the flexible OSS enabled instrument is employed to sense a shape of the optical fiber.

Figure 11:
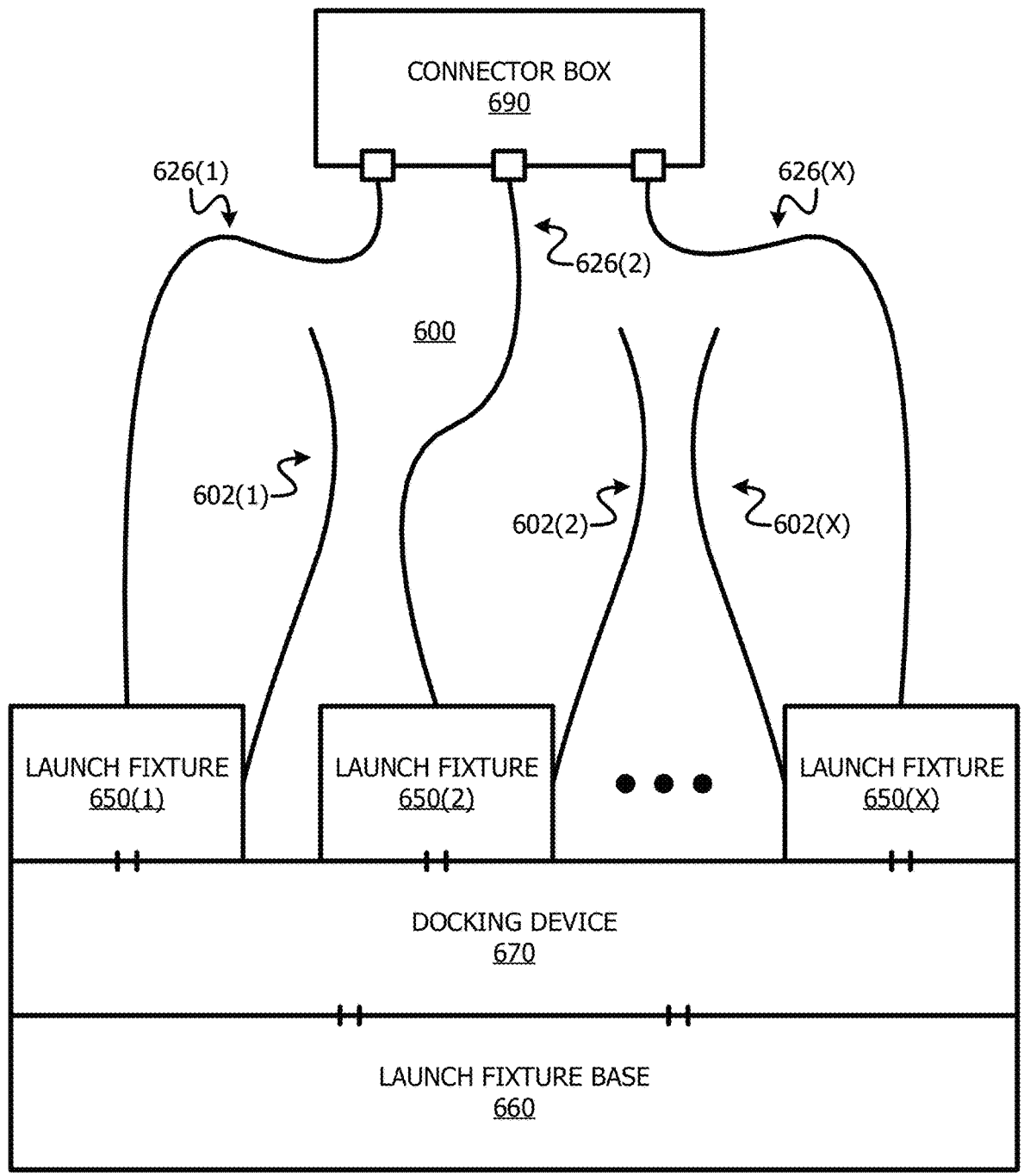
FIG. 11 is a block diagram showing a shape sensing system which employs launch fixture(s) with controlled fiber positioning and a docking device for securing launch fixture(s) to a launch fixture base in accordance with one embodiment.

Referring to FIG. 11, in practice, the present disclosure provides a capability of using a fixation assembly of the present disclosure on one side or both sides of an operating table, while minimizing the constraints on the "free" part of the optical cables fixed to the launch fixture (i.e., the portion of the cable bridging the launch fixture to the portion of the OSS enabled instrument to be inserted in the patient body). Such constraints may appear if the bending of these cables is too important, in general or locally, or if the cables are twisted etc., which could lead to performance loss in general (e.g., a problem of registration or a problem of undesired movement of the cables during operation). Thus, it is desirable to minimize those constraints while having the possibility to mount the fixture assembly one or other side of the operating table.

To thereby minimize the constraints, the embodiment of the present disclosure as shown in FIG. 11 provides an additional component to the launch assembly 600 in the form of a docking device 670 serving as an intermediate piece between an X number of launch fixtures 650, $X \geq 1$ and a launch fixture base 660 for securing the launch fixture(s) 650 onto the launch fixture base 660.

In practice, a purpose of docking device 670 is to provide a sterile fixation for the launch fixture(s) 650. More particularly as will be further described in the present disclosure, a sterile patient drape (not shown) may be placed on top of the launch fixture base 660, whereupon the docking device 670 is placed. Moreover, as will be further described in the present disclosure, a design of the docking device 670 may be reversible and ensures the exit angle of the launch reduces the issues as mentioned above. Each launch fixture 650 is an embodiment of the launch fixtures 150 of FIG. 1, whereby each launch fixture 650 receives and secures an optical fiber 626 and a flexible OSS instrument 602 having optical fiber embedded therein. For this embodiment, each optical fiber 626 is connected to a connector box 690 to an interrogator (not shown).

In practice, as will be exemplary shown in more detail herein, docking device 670 may have one or more sides connectable to the launch fixture base 660 whereby the launch fixtures 650 are installable into opposing side(s) of docking device 670.

Also in practice, as will be exemplary shown in more detail herein, docking device 670 may be detachable connectable to launch fixture base 660 (e.g., clipped thereto) and docking device 670 may include fixing element(s) (not shown) arranged on one side or on two opposing sides of the docking device 670 to detachably fix the docking device 670 to the launch fixture base 660.

In practice, for embodiments having fixing element(s) (not shown) on two opposing sides of the docking device 670, the fixing elements must be arranged for alignment with the launch fixture base 660 for either side.

More particularly, in one embodiment, a geometry and a location of these fixing element(s) are symmetrical with respect to a transversal plane of the docking device 670 (e.g., transversal plane being perpendicular to an operating table) such that the docking device 670 can still be fixed to the launch fixture base 660 even after a 180° rotation about an axis perpendicular to the main axis of the operating table (i.e., an "upside down-ability" fixation). Alternatively, a geometry and a location of these fixing element(s) may be non-symmetrical with respect to a transversal plane of the docking device 670 (e.g., a rotationally symmetry around a short axis of an operating table plane), and a geometry and a location of these fixing element(s) may be symmetrical with respect to a transversal plane of the docking device 670 without a rotational symmetrical around the axis perpendicular to the main axis of the operating table.

Further in practice, as will be exemplary shown in more detail herein, docking device 670 may employ one or more connecting through-slots (not shown) to receive the launch fixture(s) 650, with a symmetry regarding the geometry of these connecting slots with respect to a longitudinal plane (e.g., longitudinal plane being parallel to an operating table), this symmetry involves in particular symmetry of the locations and geometries of connecting protrusions extending from the internal walls of the slots, in order to be able to clip the launch fixture(s) 650 both from the top and from the bottom of the connecting slots (and the same for the connectors provided on top of the launch fixture base 660 if any).

In one embodiment, as will be exemplary shown in more detail herein, the connecting slots are angled with respect to the main axis of an operating table, in such a way that the mechanical constraints on the optical fiber(s) 626 clamped to the launch fixture(s) 650 are minimized. The rotation of the docking device 670 as previously explained allows keeping the angle of the connecting slots with respect to the main axis of the operating table to thereby minimize constraints on optical fibers 626 if the launch fixture base 660 and docking device 670 are positioned on the other side of the operating table without changing the position of the patient on the operating table. This feature is advantageous for surgeons/clinicians.

Optionally in practice, a label may be provided on both main surfaces of the docking device 670 indicating the right positioning of the docking device 670 with respect to a position of a patient (e.g. that could be a schematic representation of the patient: position of the head), which may help the technician (or the surgeon) to position the docking device 670 (or the patient) in a correct position with respect to the position of the patient (or to the position of the docking device 670).

Also optionally in practice, the docking device 670 may be provided as a sterile component, and the design of the launch fixture base 660 may allow for a drape (not shown) to be arranged between the launch fixture base 660 and the docking device 670 while still fixing the docking device 670 properly, whereby the sterile instruments 602 would be connected to a corresponding launch fixture 650 to a sterile docking device 670. A tether (not shown) leading from a launch fixture 650 to the non-sterile connector box 690 may be used to bridge the sterile barrier.

Further optionally in practice, at least 2 indicators of different colors, one color provided to a launch fixture 650 of one type of instrument 602 (e.g., a catheter) and one color provided to another launch fixture 650 of a different type of instrument 602 (e.g., a guidewire) may be used as the respective virtual representations of the instruments 602 (e.g., catheter & guidewire) on a display (not shown). The actual indicators being located on the launch fixture(s) to be easily seen by the user during operation and while he/she is watching the display.

Additionally optionally in practice, a marker may be provided on a rail of an operating table to position the launch fixture base 660 at the right position to minimize strains on the optical fiber 626. Several markers may be provided depending on the length of the optical fibers 626.

Even further in practice, as will be exemplary shown in more detail herein, each launch fixture 650 may employ a radio frequency identification (RFID) tag identifying a type of OSS enabled instrument 602 (e.g., a catheter or a guidewire) secured by the launch fixture 650 and launch fixture base 660 may employ a RFID antenna to thereby sense the RFID tag(s) of the launch fixture(s) 650. Furthermore, a connector of each launch fixture 650 may employ a RFID tag identifying that particular launch fixture 650 and connector box 690 may employ a RFID antenna to thereby sense the RFID tag(s) of the connectors.

In one embodiment, connection box 690 includes a RFID controller including an RFID antenna for sensing the RFID tag(s) of the fixture connectors to thereby distinguish between the launch fixture(s) 650. Additionally, the RFID controller may be in communication with the RFID antenna of the launch fixture base 660 thereby support a displayed color representation of the type of OSS enabled instrument 602 for each launch fixture 650.

Various embodiments of launch fixture 650, launch fixture base 660 and docking device 670 as shown in FIGS. 12A-20E will now be described herein.

Figure 12A:
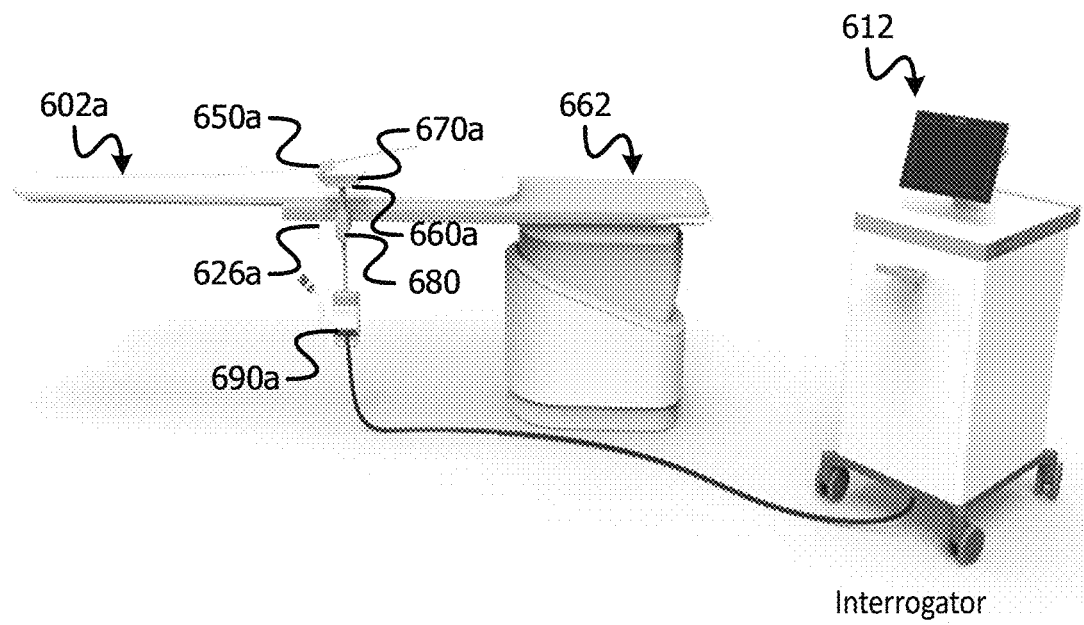
FIG. 12A is a side view of the shape sensing system of FIG. 11 deployed in an operating environment in accordance with one embodiment.

Referring to FIG. 12A, a launch fixture base 660*a* is connected via a table clamp 680 onto an operating table 662, and a docking station 670*a* secures a launch fixture 650*a* onto launch fixture base 660*a*. Launch fixture 650*a* receives and secures an optical fiber 626*a* and a flexible OSS instrument 602*a*. The optical fiber 626*a* is connectable to a connector box 690*a* for a signal connection to an interrogator workstation 612.

Figure 12B:
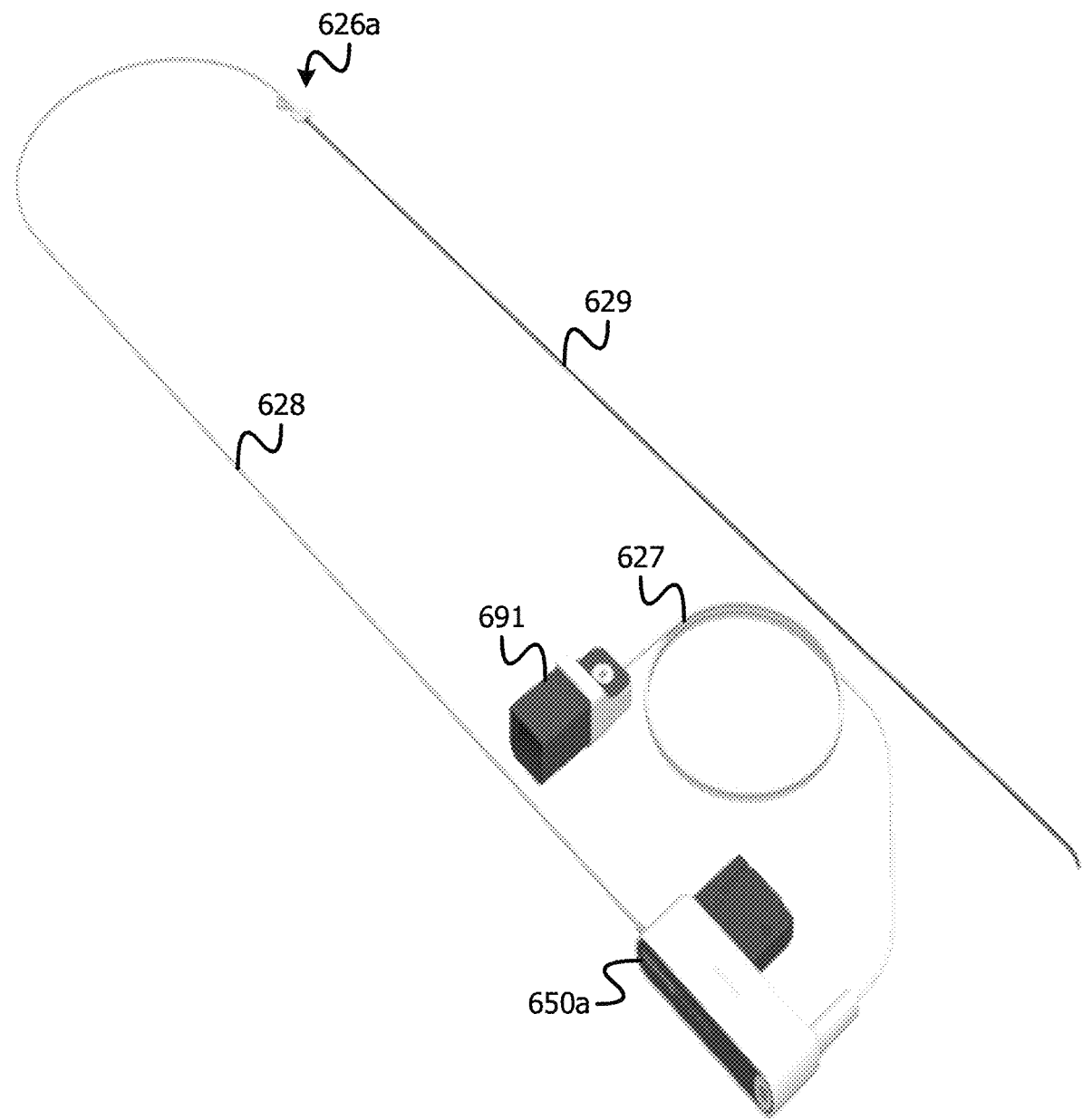
FIG. 12B is a perspective view of the optical fiber of FIG. 12A.

Referring to FIG. 12B, a free section 627 of optical fiber 626*a* has one end within a connector 691 and another end received and secured within launch fixture 650*a*. A torque absorbing section 628 of optical fiber 626*a* (aka a joining section) has one end secured within launch fixture 650*a* and another end adjacent with an in-body section 629 of optical fiber 626*a*. A torque absorbing section 628 of optical fiber 626*a* decouples rotation of in-body section 629 from launch fixture 650 as fixed by the docking device 670*a*.

Figure 13A:
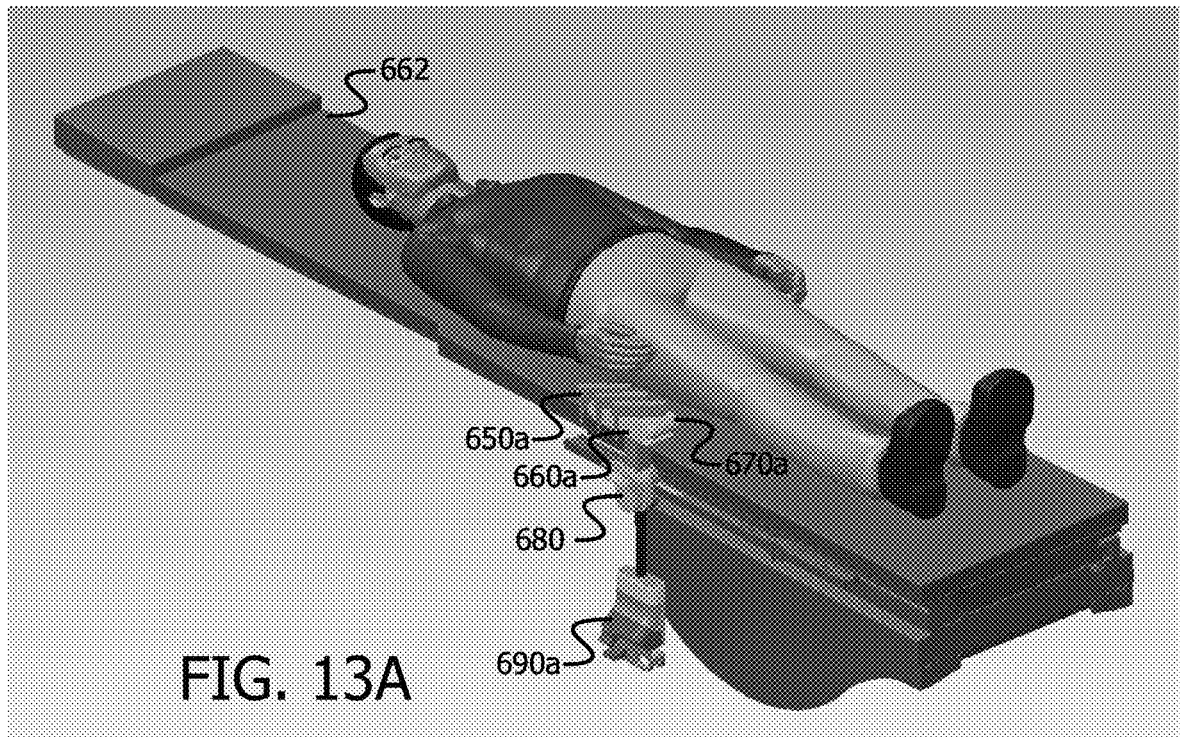
FIGS. 13A and 13B are views of the shape sensing system of FIG. 11 relative to a patient in an operating environment in accordance with one embodiment.
Figure 13B:
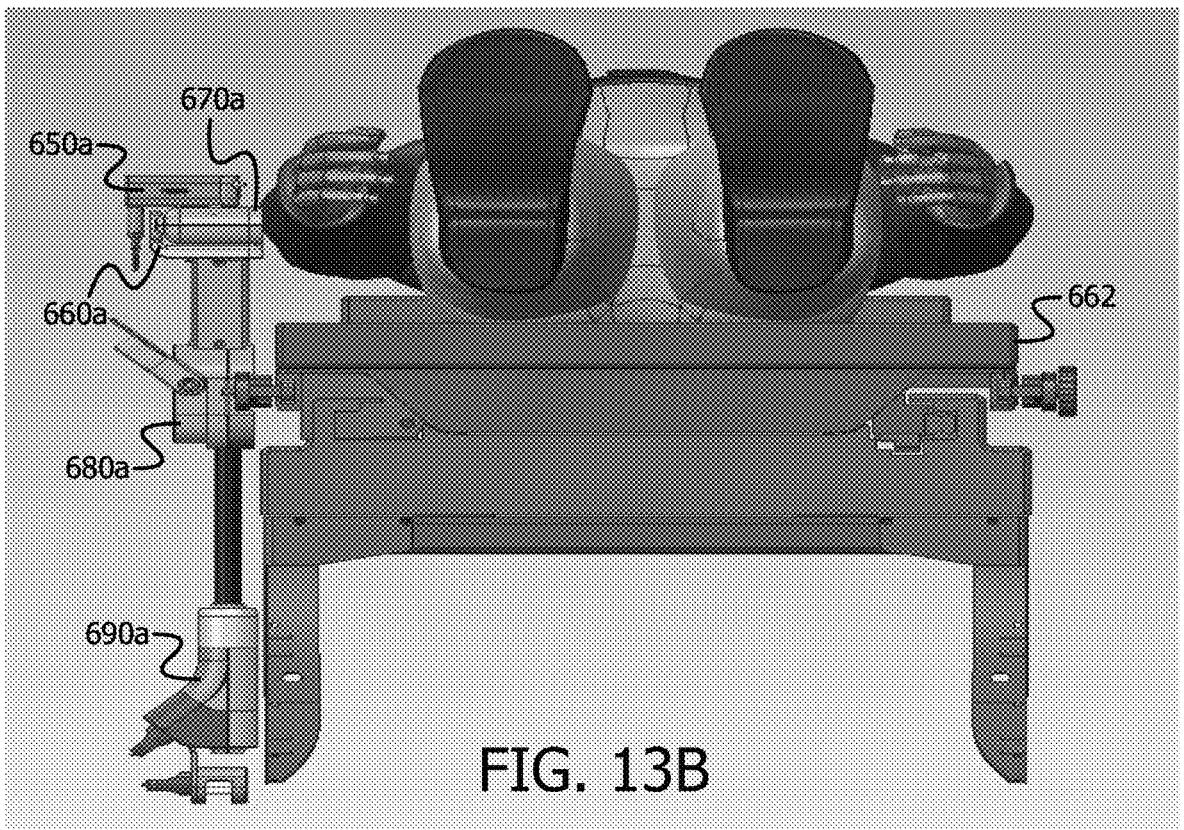

Referring to FIGS. 13A and 13B, a representation of FIG. 12A is shown docking device 670*a* detachably connected to launch fixture base 660*a* (e.g., clipped thereto) and docking device 670*a* including fixing element(s) (not shown) arranged on one side of the docking device 670*a* to detachably fix the docking device 670*a* to the launch fixture base 660. A geometry and a location of these fixing element(s) are symmetrical with respect to a transversal plane of the docking device 670*a* (e.g., transversal plane being perpendicular to an operating table 662) such that the docking device 670*a* can still be fixed to the launch fixture base 660*a* even after a 180° rotation about an axis perpendicular to the main axis of the operating table 662 (i.e., an "upside down-ability" fixation).

Docking device 670*a* employs three (3) connecting through-slots to receive three (3) launch fixtures 650, with a symmetry regarding the geometry of these connecting slots with respect to a longitudinal plane (e.g., longitudinal plane being parallel to an operating table 662), this symmetry involves in particular symmetry of the locations and geometries of connecting protrusions extending from the internal walls of the slots, in order to be able to clip the launch fixture(s) 650*a* both from the top and from the bottom of the connecting slots (and the same for the connectors provided on top of the launch fixture base 660*a* if any).

The connecting slots are angled with respect to the main axis of an operating table 662, in such a way that the mechanical constraints on the optical fibers 626 clamped to the launch fixtures 650*a* are minimized. The rotation of the docking device 670*a* as will in more explained herein allows keeping the angle of the connecting slots with respect to the main axis of the operating table 662 to thereby minimize constraints on optical fibers 626 if the launch fixture base 660*a* and docking device 670*a* are positioned on the other side of the operating table 662 without changing the position of the patient on the operating table 662. This feature is advantageous for surgeons/clinicians.

In practice, a docking device 670 may employ one or more connecting through-slots and docking device 670 includes a RFID reader per slot for reading a RFID tag of the launch fixture(s) 650.

Figure 14A:
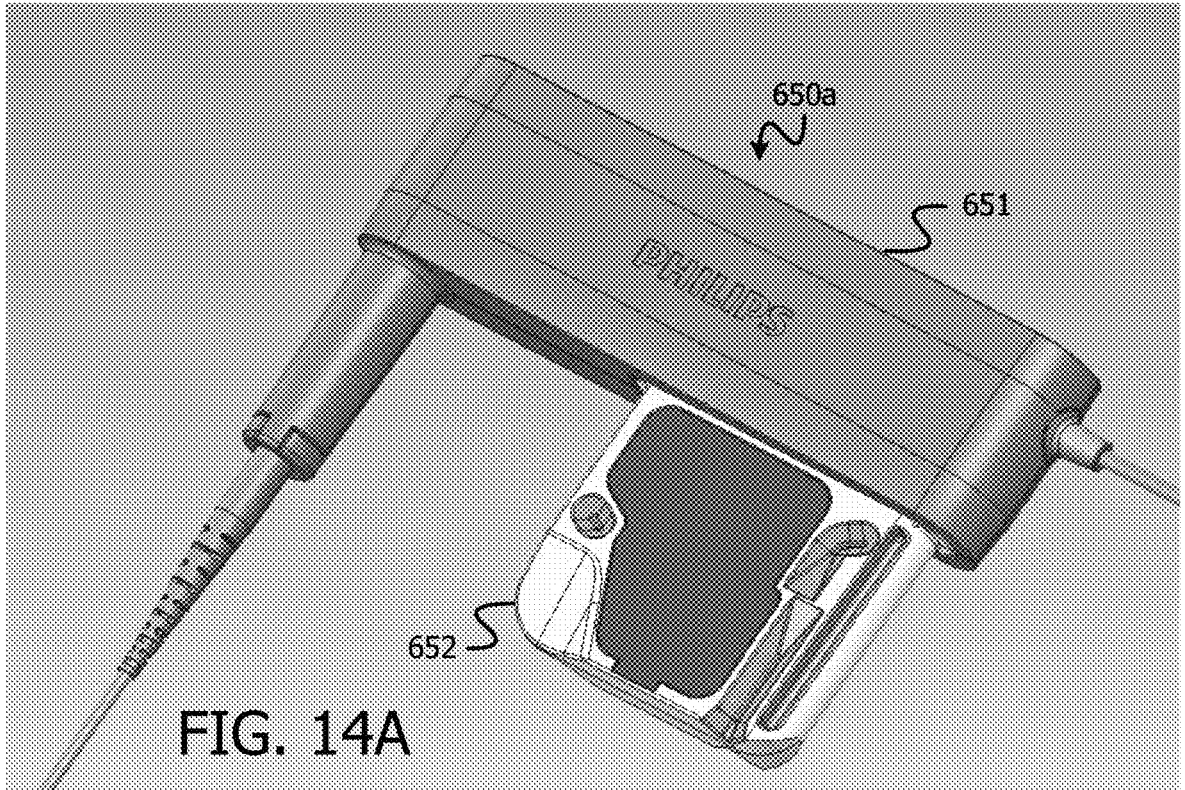
FIGS. 14A and 14B are perspective views of a launch fixture with controlled fiber positioning in accordance with one embodiment.
Figure 14B:
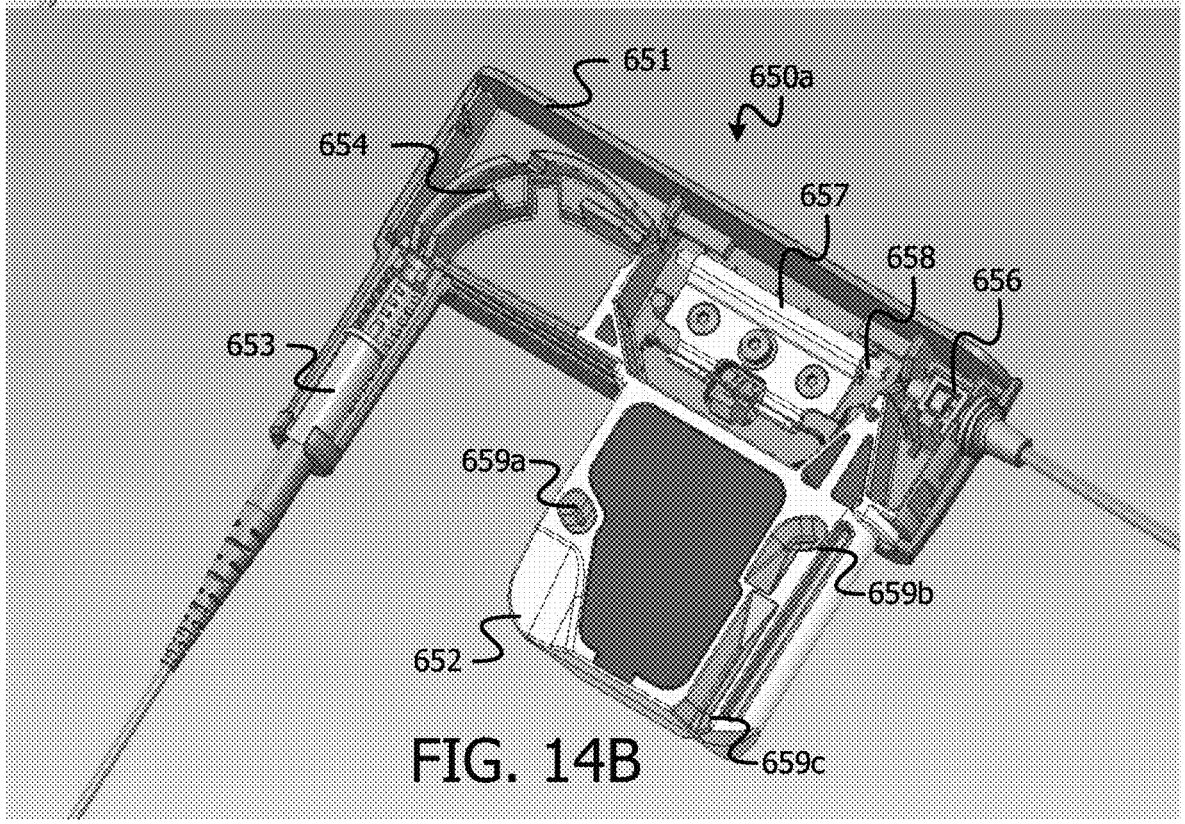

Referring to FIGS. 14A and 14B, launch fixture 650*a* has a housing 651 and a docking interface 652.

Housing 651 includes a fixation device 653 configured to receive and secure an optical fiber, a fiber storage area 654 configured to receive and maintain the optical fiber within specified dimensions, a fixation device 656 configured to receive and secure a flexible OSS enabled instrument, and a launch region 657 configured to receive and maintain the optical fiber in a known geometric configuration before entering the second fixation device.

Figure 14C:
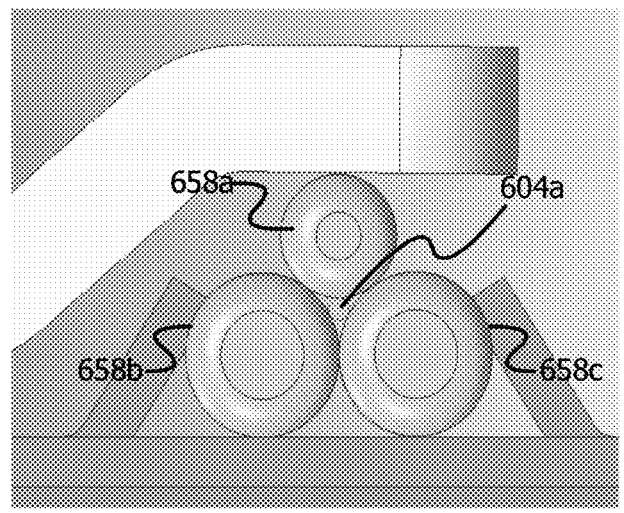
FIG. 14C is a view of a fiber clamp of the launch fixture of FIGS. 14A and 14B in accordance with one embodiment.

Launch region 657 includes three (3) shafts 658a-658c as shown in FIG. 14C to clamp the optical fiber.

Docking interface 652 includes a series of slots 659a-659c for connecting to a launch fixture slot of docking device 670a.

Figure 15A:
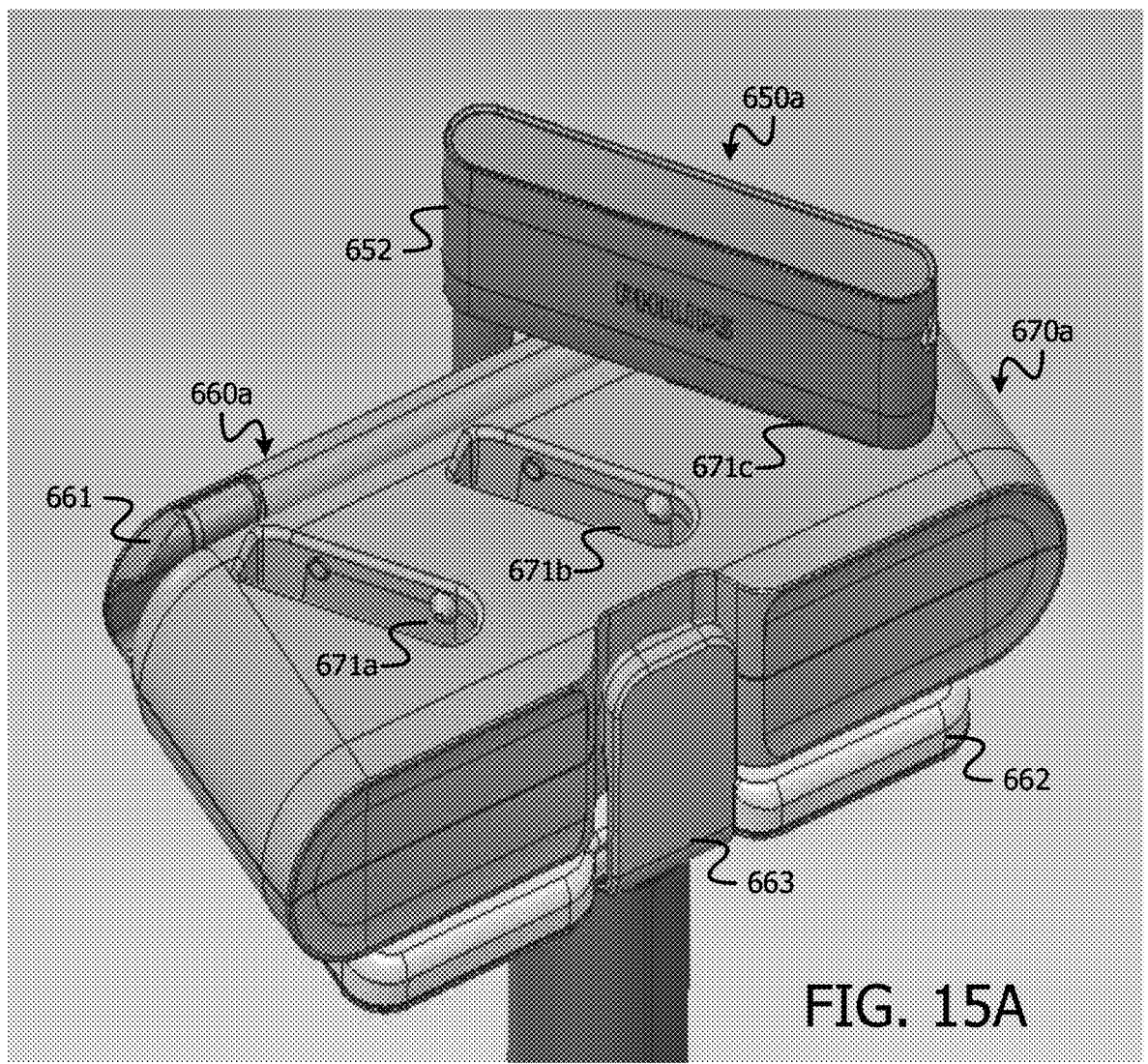
FIG. 15A-15C are perspective views of the launch fixture of FIGS. 13A and 13B secured onto a launch fixture base via a docking device in accordance with one embodiment.
Figure 15B:
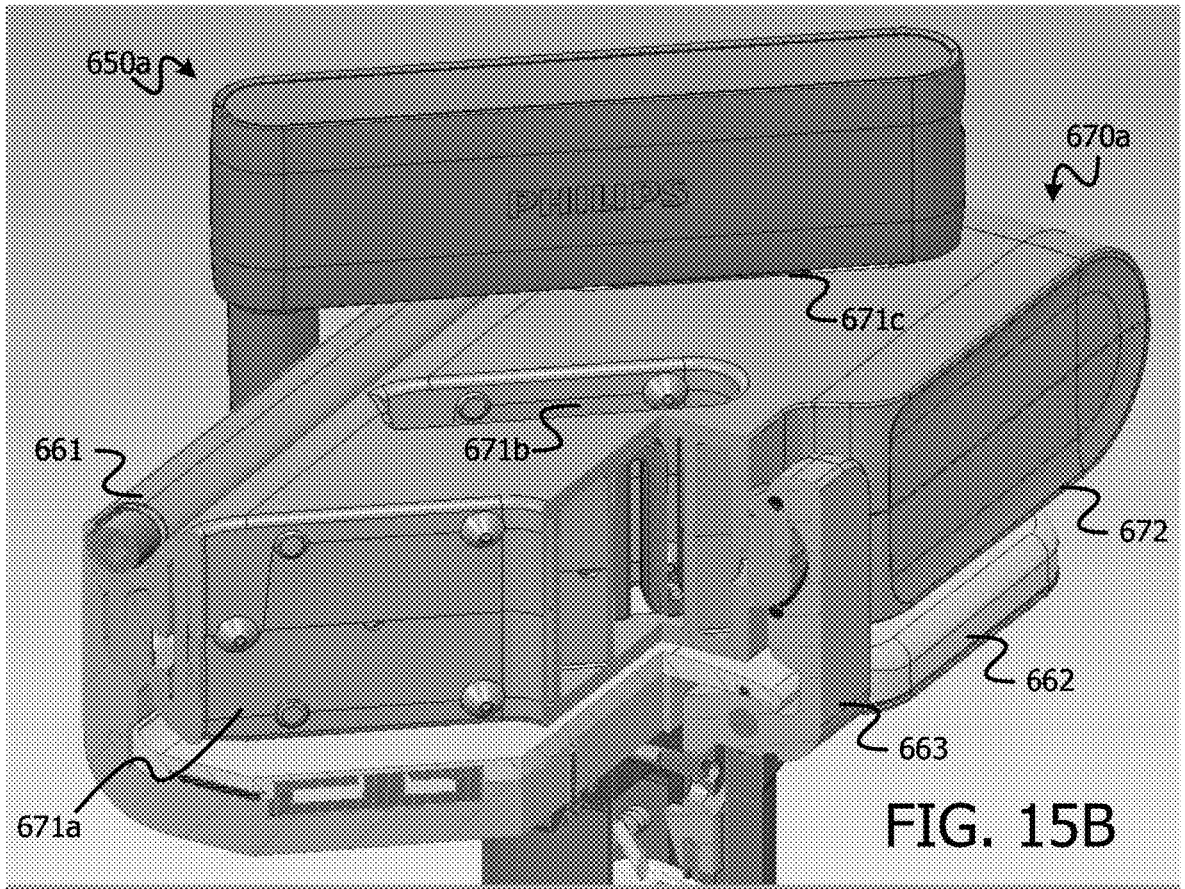
Figure 15C:
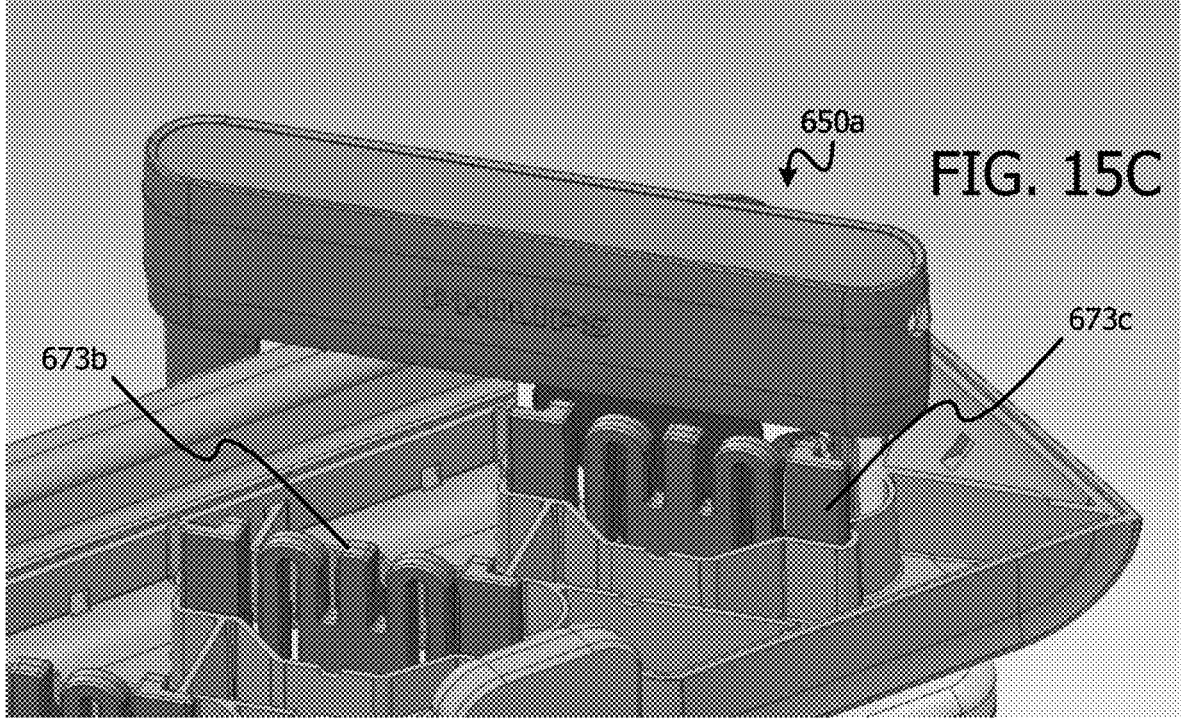

Referring to FIGS. 15A-15C, the docking interface 652 of launch fixtures 650 are inserted within launch fixture slots 671a-671c of docking device 670a. Each slot 671a-671c employs a base interface (e.g., base interfaces 673b and 673c shown in FIG. 15C) for interfacing with the docking interfaces 652. Additionally, launch fixture base 660a has an upright standing wall 661 and a base 662 for interconnecting with docking device 670a via fixing elements (not shown) between base 662 and docking device 670a.

Referring to FIG. 16, the docking device 670a may be provided as a sterile component, and the design of the launch fixture base 660a may allow for a drape 700 to be arranged between the launch fixture base 660a and the docking device 670a to form a bridge between a sterile zone 700 and a un-sterile zone 701 while still fixing the docking device 670a properly. For this embodiment, the sterile instruments 602 would be connected to a corresponding launch fixture 650a to a sterile docking device 670. A tether (not shown) leading from a launch fixture 650a to the non-sterile connector box 690a (FIG. 11) may be used to bridge the sterile barrier formed by drape 700. Also, as shown in FIG. 17, a clamp force applied by torsion spring 664 to have high force in clamp position of docking device 670a (FIG. 15B) on launch fixture base 680a and the force lowers when opening to thereby minimize damage to drape 700.

Referring to FIGS. 18A-18C, table clamp 680 employs a lever 681, a spring 682, an arm 683 and a stop 684. Lever 681 is operated to rotate arm 683 against the force of spring 682 to enable a positioning of a rail 663 of operating table 662 between arm 683 and stop 684. Lever 681 is released to enable the force of spring 682 to securely clamp rail 663 between arm 683 and stop 684. In practice, the force needed to open the table clamp 680 does not increase by using an optimized curve.

Figure 19A:
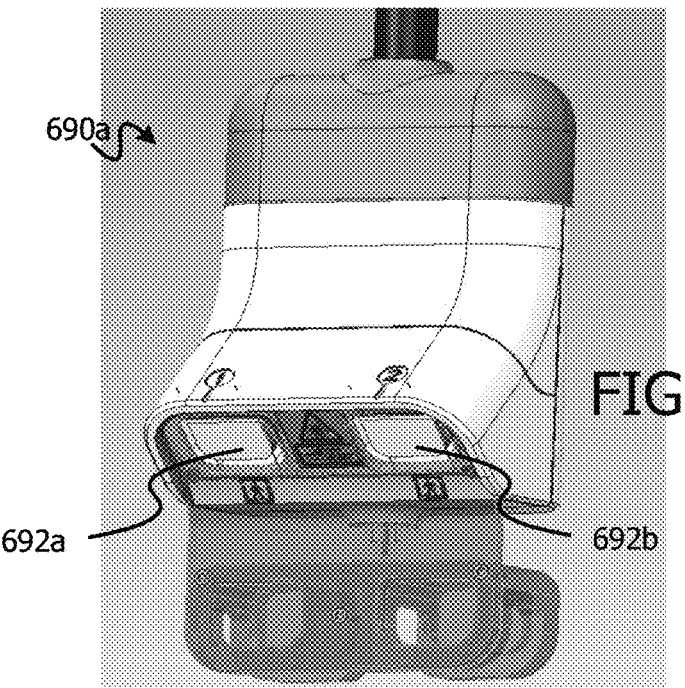
FIGS. 19A-19C are a perspective view and exploded views, respectively of a connection box in accordance with one embodiment.
Figure 19B:
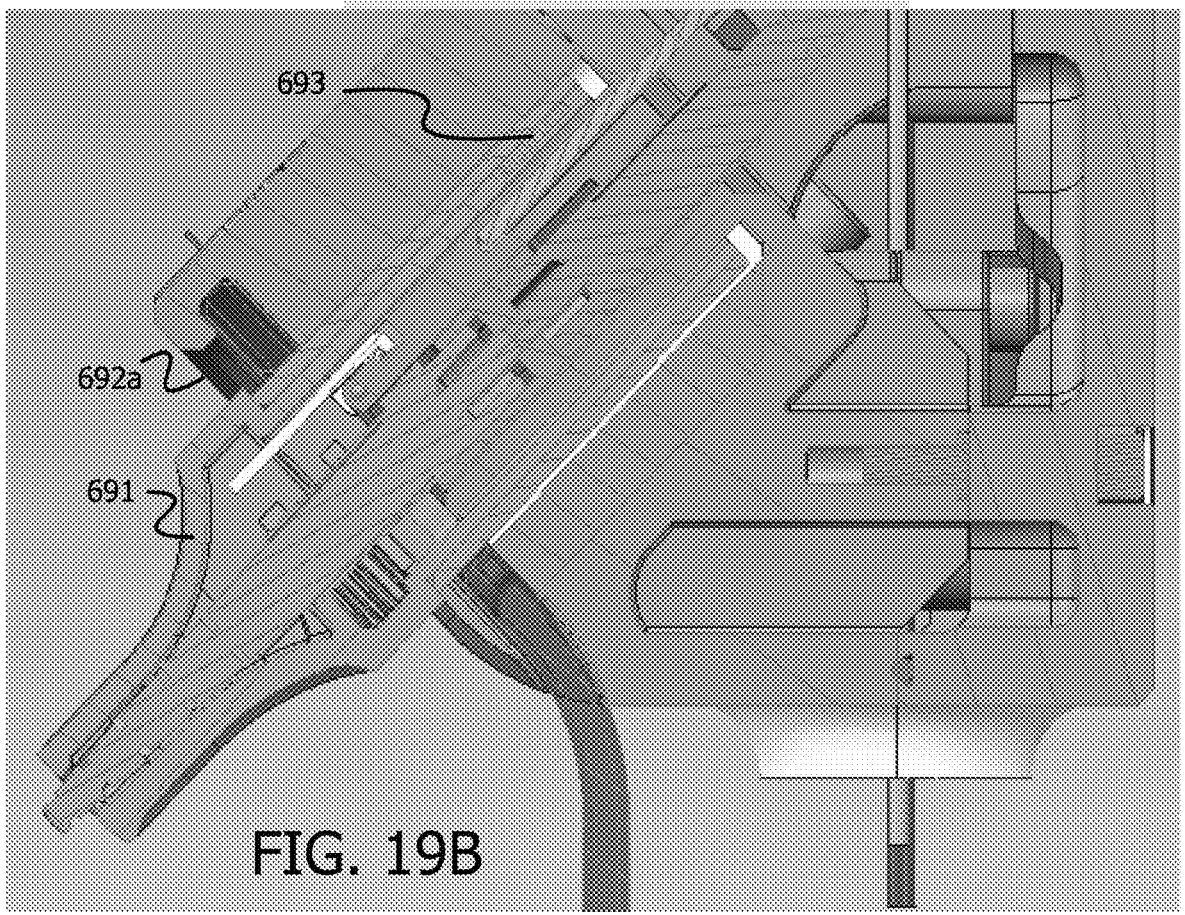
Figure 19C:
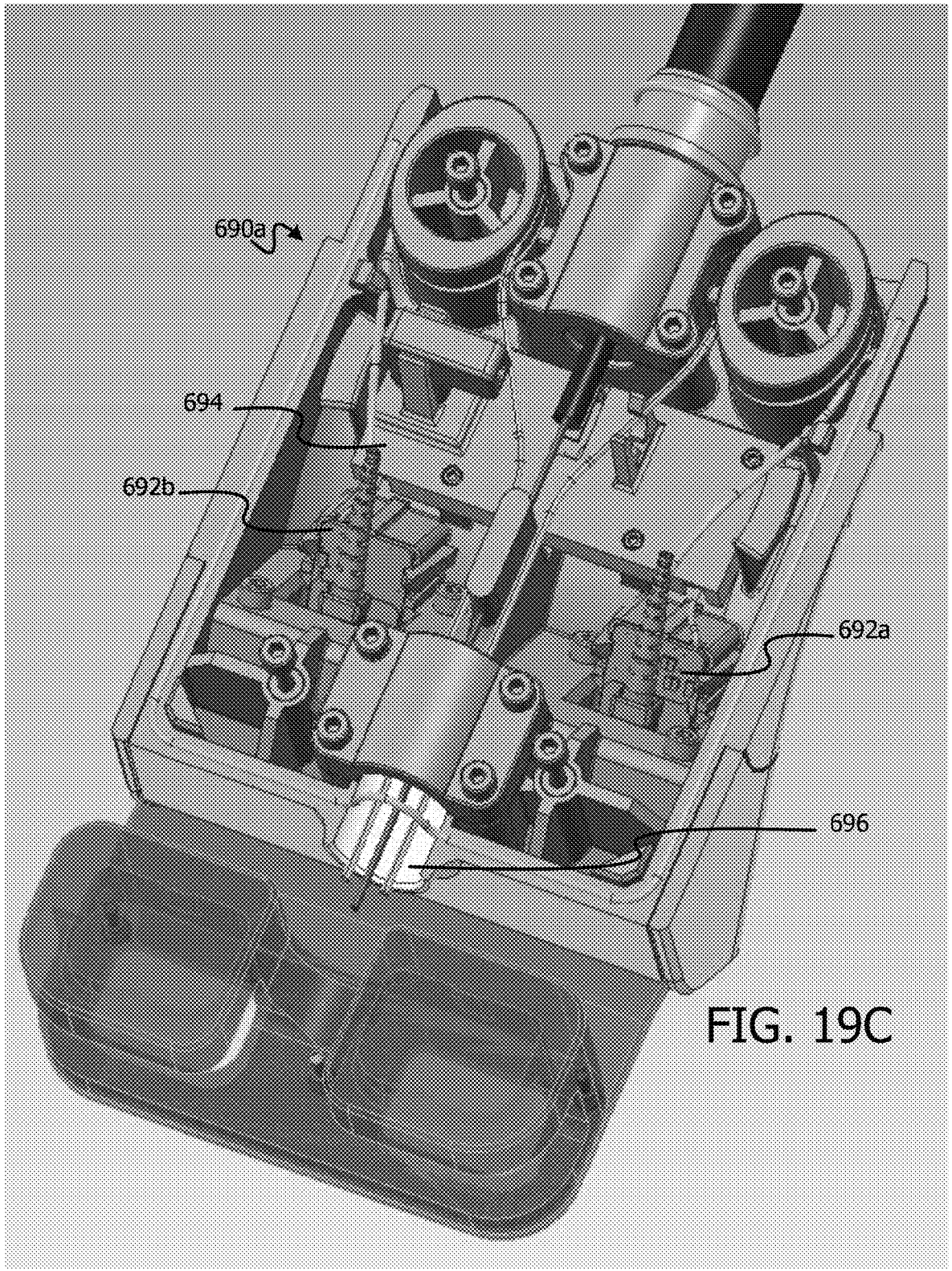

Referring to FIGS. 19A-19C, connector box 690a has two (2) outlets 692a and 692b for connector 691 (FIG. 12). As shown in a side view of FIG. 19B, when inserted in an outlet 692 (e.g., outlet 692a), connector 691 includes a RFID 693 for identifying the type of instrument 602 (FIG. 11). As shown in a rear view of FIG. 19C, outlets 692a and 692b and a RFID controller 694 are connected to interrogator workstation 612 (FIG. 12A) via a series 693 of optical fibers and communication wire.

Figure 20A:
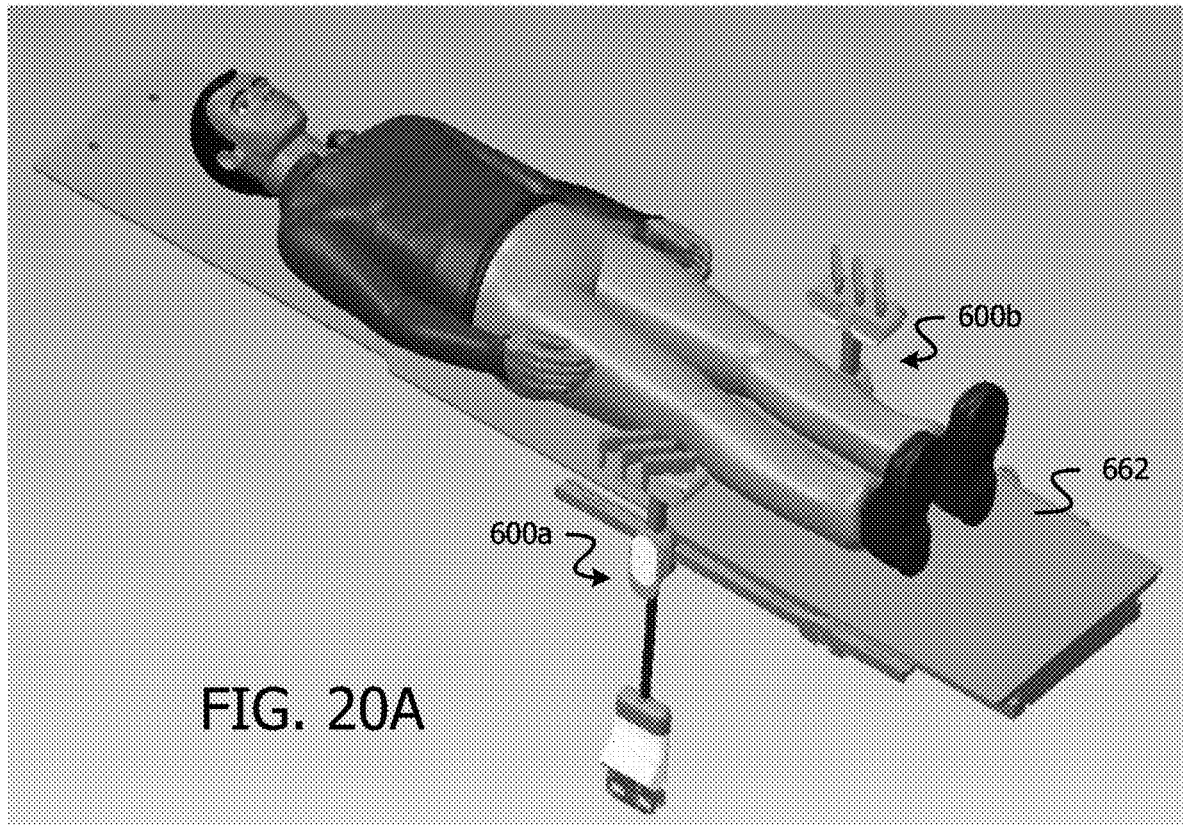
Figure 20B:
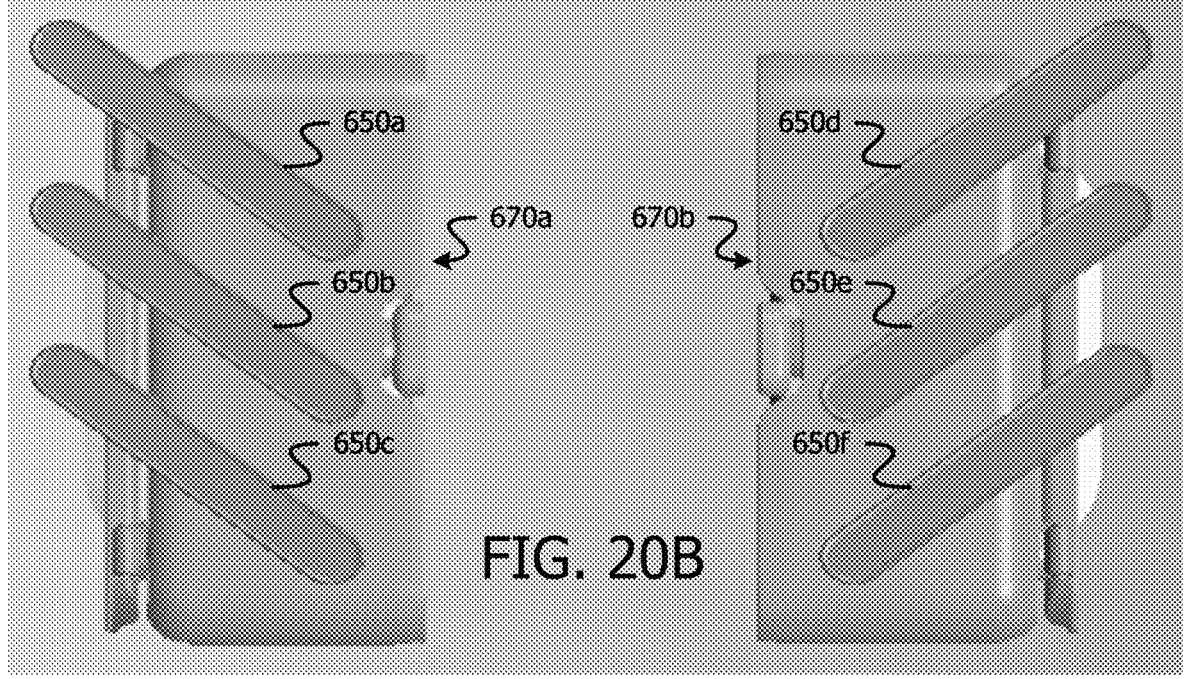

To facilitate an understanding of the reversible nature of a docking device of the present disclosure, FIG. 20A shows a launch assembly 600a and a launch assembly 600b attached to opposing sides of operating table 662. As shown in FIGS. 20B-20E, a docking device 670a of launch assembly 600a is supporting three (3) launch fixtures 650a-650c, and a docking device 670b of launch assembly 600b is supporting three (3) launch fixtures 650d-650f.

Figure 20E:
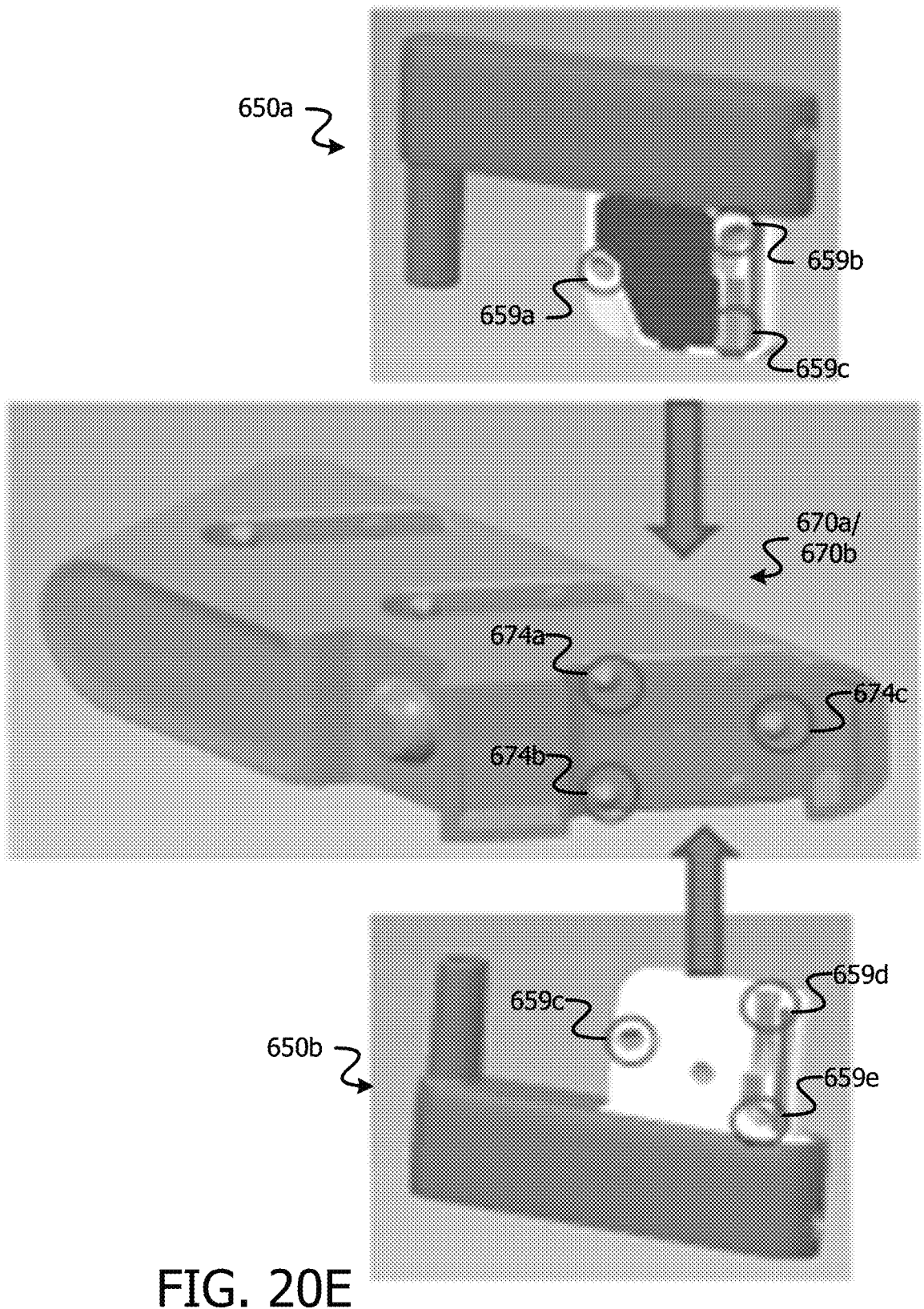

The connecting slots 671 of the docking devices 670 are angled with respect to the main axis of an operating table 662, in such a way that the mechanical constraints on the optical fiber(s) (not shown) clamped to the launch fixture(s) 650 will be minimized. As such, as shown in FIG. 20E, docking device 670b is a rotation of docking device 670a that allows keeping the angle of the connecting slots 671 with respect to the main axis of the operating table 662 to thereby minimize constraints on optical fibers (not shown) if the launch fixture base 660 and docking device 670 are positioned on the other side of the operating table 662 without changing the position of the patient on the operating table 662. This feature is advantageous for surgeons/clinicians. In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments a launch fixture for optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An optical shape sensing (OSS) system, comprising:
a launch fixture configured to receive and secure an optical fiber within a flexible OSS enabled instrument, wherein the launch fixture comprises a docking interface integrated with and extending from the launch fixture;
a launch fixture base configured to be connected to a support structure; and
a docking device configured to secure the launch fixture onto the launch fixture base, wherein the docking device comprises a launch fixture slot passing through the docking device, wherein the launch fixture slot is configured to receive and secure the docking interface of the launch fixture through a top side of the docking device and alternatively through an opposing bottom side of the docking device.

2. The system as recited in claim 1, wherein the launch fixture includes:
a first fixation device configured to receive and secure the optical fiber;
a fiber storage area configured to receive and maintain the optical fiber within specified dimensions; and
a second fixation device configured to receive and secure the flexible OSS enabled instrument.

3. The system as recited in claim 2, wherein the launch fixture includes:
a launch region configured to receive and maintain the optical fiber in a known geometric configuration before entering the second fixation device; and
a defined path enabling correction for rotation of the launch region.

4. The system as recited in claim 1, wherein the docking device includes a plurality of connectors arranged to detachably fix the docking device to the launch fixture base.

5. The system as recited in claim 4, wherein a geometry and a location of the plurality of connectors are symmetrically arranged on one of the top side or the opposing bottom side of the docking device.

6. The system as recited in claim 1, wherein the launch fixture includes a radio frequency identification associated with a type of the flexible OSS enabled instrument.

7. The system as recited in claim 6, further comprising:
a controller configured to recognize the radio frequency identification of the flexible OSS enabled instrument.

8. The system as recited in claim 1, further comprising:
a display configured to display a virtual representation of the flexible OSS enable instrument based on an identification included on the launch fixture associated with the virtual representation.

9. The system as recited in claim 1, further comprising:
a sterile drape arranged between the docking device and the launch fixture base when the docking device is securing the launch fixture onto the launch fixture base.

10. The system as recited in claim 1, wherein the launch fixture slot is slanted at an angle relative to a main axis of the support structure that reduces mechanical constraints on the optical fiber.

11. An optical shape sensing (OSS) system, comprising:
a plurality of launch fixtures configured to receive and secure optical fibers within a plurality of flexible OSS enabled instruments, respectively, wherein the plurality of launch fixtures comprise a plurality of docking interfaces integrated with and extending from the plurality of launch fixtures, respectively;
a launch fixture base configured to be connected to a support structure; and
a docking device configured to secure the plurality of launch fixtures onto the launch fixture base, wherein the docking device comprises a plurality of slots passing through the docking device, wherein the plurality of slots are configured to be able to receive and secure the plurality of docking interfaces of the plurality of launch fixtures, respectively, inserted through a top side of the docking device and alternatively inserted through an opposing bottom side of the docking device.

12. The system as recited in claim 11, wherein the plurality of slots are symmetrically arranged on each of the top side and the opposing bottom side of the docking device.

13. The system as recited in claim 11, wherein the plurality of slots are slanted at an angle relative to a main axis of the support structure, reducing mechanical constraints on the optical fibers.

14. The system as recited in claim 11, wherein the plurality of launch fixtures include identifications associated with types of the flexible OSS enabled instruments, respectively.

15. The system as recited in claim 14, wherein the identifications are radio frequency identifications.

16. The system as recited in claim 11, wherein the plurality of launch fixtures include identifications associated with virtual representations of the flexible OSS enable instruments, respectively, wherein the system further comprises:
a display configured to display the virtual representations of the flexible OSS enable instruments based on the identifications.

17. The system as recited in claim 11, further comprising:
a sterile drape arranged between the docking device and the launch fixture base when the docking device is securing the plurality of launch fixtures onto the launch fixture base.

18. An optical shape sensing (OSS) system, comprising:
a launch fixture configured to receive and secure an optical fiber within a flexible OSS enabled instrument, wherein the launch fixture comprises a docking interface integrated with and extending from the launch fixture;
a launch fixture base attachable to a structure of a patient table at a plurality of known locations, enabling registration of the launch fixture to a patient coordinate frame of reference and/or an imaging frame of reference; and
a docking device configured to secure the launch fixture onto the launch fixture base, wherein the docking device comprises a launch fixture slot passing through the docking device,
wherein the launch fixture slot is configured to be able to receive and secure the docking interface of the launch fixture inserted through either of two sides of the docking device.

19. The system of claim 18, wherein the launch fixture base maintains a defined geometric relationship with a frame of reference of the structure such that re-registration of another launch fixture to the patient coordinate frame of reference and/or the imaging frame of reference is not required when another docking interface of the another launch fixture is received and secured in the launch fixture slot in place of the launch fixture.

20. The system as recited in claim 18, wherein the docking device includes at least one connector having a geometry and a location symmetrical with respect to a transversal plane of the docking device, wherein the transversal plane is perpendicular to the patient table, such that the docking device is fixable to the launch fixture base after rotation about an axis perpendicular to a main axis of the patient table.

* * * * *